(12) United States Patent
Whitehurst et al.

(10) Patent No.: US 7,151,961 B1
(45) Date of Patent: Dec. 19, 2006

(54) TREATMENT OF MOVEMENT DISORDERS BY BRAIN STIMULATION

(75) Inventors: Todd K Whitehurst, Frazier Park, CA (US); James P McGivern, Stevenson Ranch, CA (US); Kelly H McClure, Simi Valley, CA (US)

(73) Assignee: Advanced Bionics Corporation, Valencia, CA (US)

( * ) Notice: Subject to any disclaimer, the term of this patent is extended or adjusted under 35 U.S.C. 154(b) by 586 days.

(21) Appl. No.: 10/428,744

(22) Filed: May 2, 2003

Related U.S. Application Data

(60) Provisional application No. 60/383,316, filed on May 24, 2002.

(51) Int. Cl.
  *A61N 1/00* (2006.01)
  *A61K 9/22* (2006.01)
  *A61M 31/00* (2006.01)

(52) U.S. Cl. .................. 607/2; 604/891.1; 604/66
(58) Field of Classification Search .................. 607/2, 607/3, 45, 48; 600/595; 604/891.1, 66
  See application file for complete search history.

(56) References Cited

U.S. PATENT DOCUMENTS

| | | | |
|---|---|---|---|
| 4,702,254 A | 10/1987 | Zabara | |
| 4,867,164 A | 9/1989 | Zabara | |
| 5,025,807 A | 6/1991 | Zabara | |
| 5,193,539 A | 3/1993 | Schulman et al. | |
| 5,193,540 A | 3/1993 | Schulman et al. | |
| 5,312,439 A | 5/1994 | Loeb | |
| 5,683,422 A | 11/1997 | Rise | |
| 5,707,396 A | 1/1998 | Benabid | |
| 5,711,316 A | 1/1998 | Elsberry et al. | |
| 5,716,377 A | 2/1998 | Rise et al. | |
| 5,792,186 A | 8/1998 | Rise | |
| 5,832,932 A | 11/1998 | Elsberry et al. | |
| 5,833,709 A | 11/1998 | Rise et al. | |
| 6,013,449 A | 1/2000 | Fischell et al. | |
| 6,051,017 A | 4/2000 | Loeb et al. | |
| 6,094,598 A | 7/2000 | Elsberry et al. | |
| 6,205,359 B1 | 3/2001 | Boveja | |
| 6,227,203 B1 * | 5/2001 | Rise et al. .................. 128/898 |
| 6,356,784 B1 | 3/2002 | Lozano et al. | |
| 6,415,184 B1 | 7/2002 | Ishikawa et al. | |
| 6,463,328 B1 | 10/2002 | John | |

(Continued)

FOREIGN PATENT DOCUMENTS

WO   WO-98/37926 A1   2/1998

(Continued)

OTHER PUBLICATIONS

Benabid, et al., "Long-Term Suppression of Tremor by Chronic Stimulation of the Ventral Intermediate Thalamic Nucleus", Lancet, vol. 337(8738), (Feb. 16, 1991), pp. 403-406.

(Continued)

*Primary Examiner*—Mark Bockelman
(74) *Attorney, Agent, or Firm*—Laura Haburay Bishop

(57) ABSTRACT

Introducing one or more stimulating drugs to the brain and/or applying electrical stimulation to the brain is used to treat movement disorders. At least one implantable system control unit (SCU) produces electrical pulses delivered via electrodes implanted in the brain and/or drug infusion pulses delivered via a catheter implanted in the brain. The stimulation is delivered to targeted brain structures to adjust the activity of those structures. In some embodiments, one or more sensed conditions are used to adjust stimulation parameters.

18 Claims, 11 Drawing Sheets

U.S. PATENT DOCUMENTS

| | | |
|---|---|---|
| 6,464,687 B1 | 10/2002 | Ishikawa et al. |
| 6,788,975 B1* | 9/2004 | Whitehurst et al. ............ 607/45 |
| 2001/0003799 A1* | 6/2001 | Boveja ......................... 607/45 |
| 2002/0013612 A1* | 1/2002 | Whitehurst ................... 607/45 |
| 2002/0161403 A1 | 10/2002 | Meadows et al. |
| 2003/0036780 A1 | 2/2003 | Barrett et al. |

FOREIGN PATENT DOCUMENTS

| | | |
|---|---|---|
| WO | WO-98/43700 A1 | 3/1998 |
| WO | WO-98/43701 A1 | 3/1998 |
| WO | WO-00/38669 A2 | 7/2000 |
| WO | WO-00/38669 A3 | 7/2000 |

OTHER PUBLICATIONS

Bradley, et al., "Activation of Group II Metabotropic Glutamate Receptors Inhibits Synaptic Excitation of the Substantia Nigra Pars Reticulata", The Journal of Neuroscience, vol. 20(9), (May 1, 2000), pp. 3085-3094.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Gill, et al. "Direct Brain Infusion of Glial Cell Line-Derived Neurotrophic Factor in Parkinson Disease", Nature Medicine, Advance Online Publication, (Mar. 31, 2003).

Handforth, et al., "Effect of Vagus Nerve Stimulation on Essential Tremor", Neurology, vol. 54 Suppl. 3, (2000), pp. A238.

Handforth, et al., "Suppression of Harmaline-Induced Tremor in Rats by Vagus Nerve Stimulation", Movement Disorders, vol. 16(1), (Jan. 2001), pp. 84-88.

Hooper, et al., "A Prospective Study of Thalamic Deep Brain Stimulation for the Treatment of Movement Disorders in Multiple Sclerosis", British Journal of Neurosurgery, vol. 16, No. 2 (Apr. 1, 2002), pp. 102-109.

Levy, et al. "Effects of Apomorphine on Subthalamic Nucleus and Globus Pallidus Internus Neurons in Patients with Parkinson's Disease." Journal of Neurophysiology, vol. 86(1), (Jul. 2001), pp. 249-260.

Stefani, et al., "Subdyskinetic Aomorphine Responses in Globus Pallidus and Subthalamus of Parkinsonian Patients: Lack of Clear Evidence for the 'Indirect Pathway'." Clinical Neurophysiology, vol. 113(1), (Jan. 2002), pp. 91-100.

Walker, et al., "Regulation of Limbic Motor Seizures by GABA and Glutamate Transmission in Nucleus Tractus Solitarius", Epilepsia, vol. 40(8), (Aug. 1999), pp. 1051-1057.

Whitehurst, McGivern, and Kuzma inventors for AB-116U; U.S. Appl. No. 10/081,820; filed Feb. 19, 2002; entitled "Fully Implantable Miniature Neurostimulator for Vagus Nerve Stimulation".

Whitehurst and McGivern inventors for AB-134U; U.S. Appl. No. 10/224,021; filed Aug. 19, 2002; entitled "Treatment of Movement Disorders by Extradural Motor Cortex Stimulation".

Whitehurst, McGivern, and Kuzma inventors for AB-210U; U.S. Appl. No. 10/057,115; filed Jan. 24, 2002; entitled "Fully Implantable Miniature Neurostimulator for Stimulation as a Therapy for Epilepsy".

Whitehurst inventor for AB-223U; U.S. Appl. No. 10/428,743; filed May 2, 2003; entitled "Treatment of Epilepsy by Brain Stimulation".

\* cited by examiner

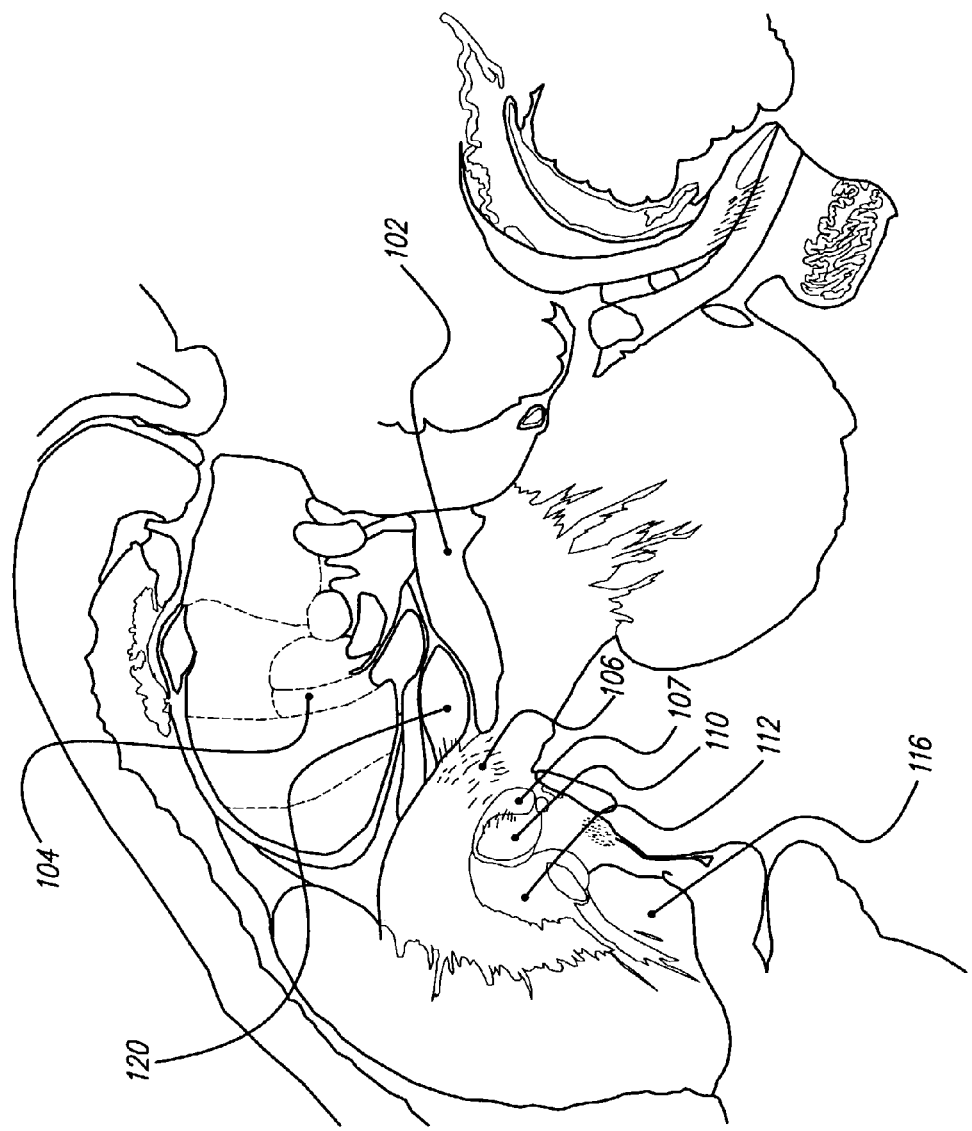

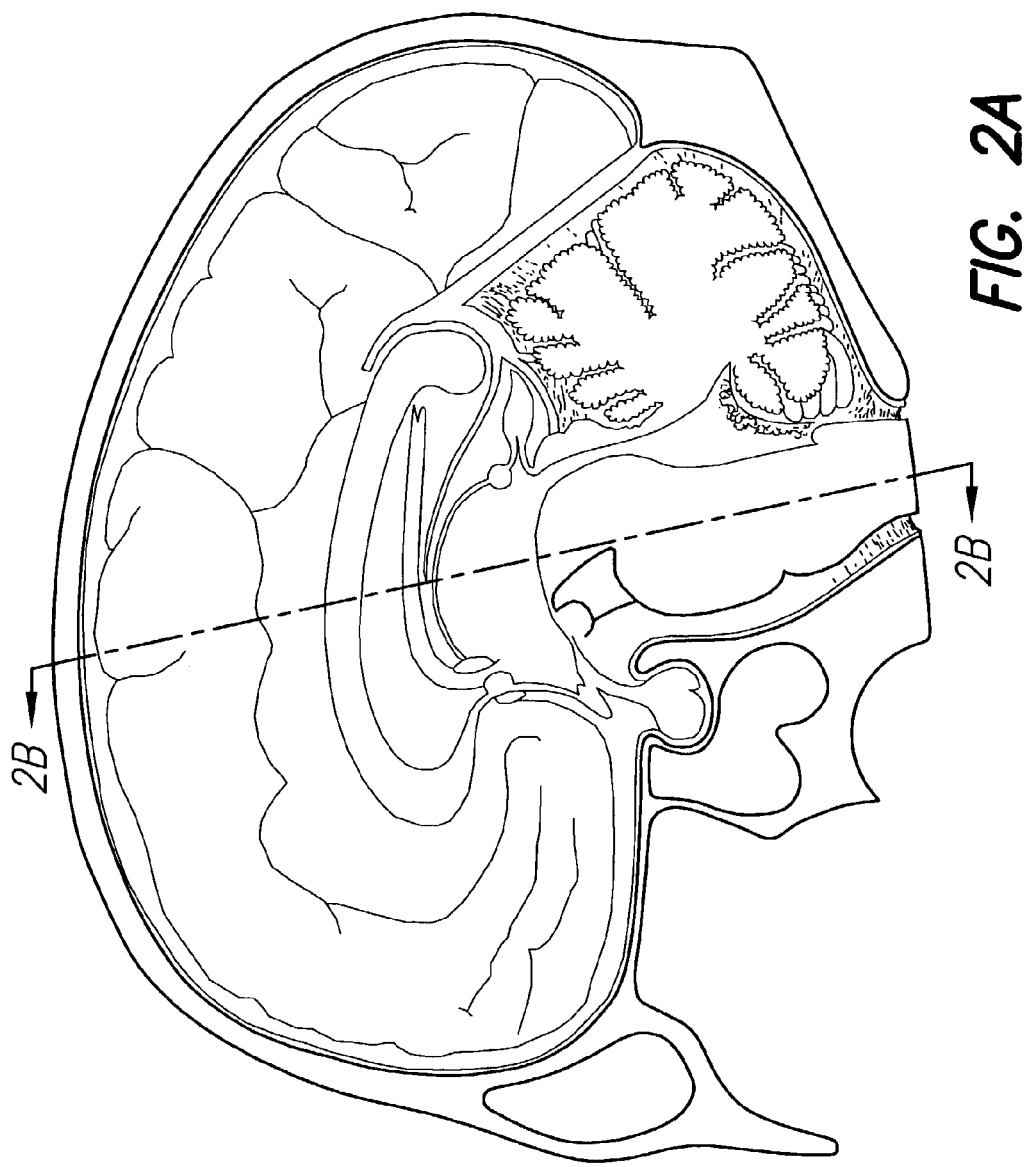

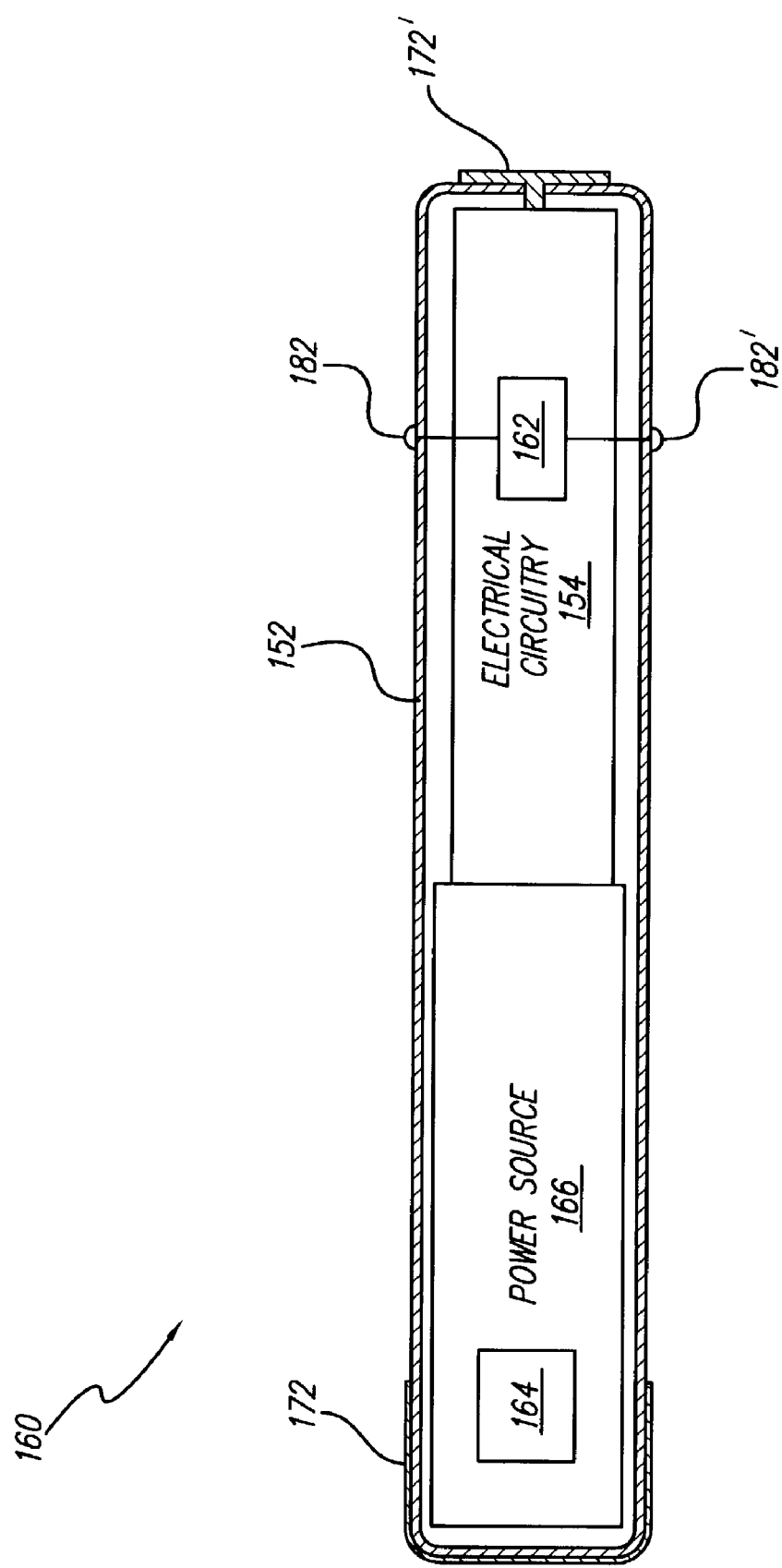

TREATMENT OF MOVEMENT DISORDERS BY BRAIN STIMULATION

The present application claims the benefit of U.S. Provisional Patent Application Ser. No. 60/383,316, filed May 24, 2002, which application is incorporated herein by reference in its entirety.

FIELD OF THE INVENTION

The present invention generally relates to implantable drug delivery and electrical stimulation systems and methods, and more particularly relates to utilizing one or more implantable devices to deliver electrical stimulation and/or one or more stimulating drugs to certain areas of the brain as a treatment for movement disorders.

BACKGROUND OF THE INVENTION

Movement disorders are neurologic syndromes characterized by either an excess or a paucity of movement. These disorders affect approximately two million Americans, including over one million suffering from benign essential tremor, and half a million suffering from Parkinson's Disease. A substantial percentage of those afflicted with movement disorders experience a significant decrease in quality of life, suffering such problems as incapacitating tremor, limited mobility, bradykinesia (difficulty consciously initiating movement), dysarthria (difficulty with speech), and consequent social isolation. The etiology of many movement disorders, e.g., benign essential tremor, is poorly understood. For other movement disorders, e.g., Parkinson's disease, the mechanism of the disorder and brain cells affected have been identified, but even with optimal care the disease may not be reversed and may even continue to progress.

Parkinson's Disease is caused by a gradual loss of dopaminergic (i.e., dopamine-secreting) neurons in the substantia nigra. Consequently, levels of dopamine decrease in the striatum (i.e., the putamen and the caudate nucleus). Although dopamine has both excitatory and inhibitory effects on the striatum, the predominant effect of the loss of dopamine is decreased inhibition (by GABA) of the internal segment of the globus pallidus. This leads to increased GABA output from the internal segment of the globus pallidus, which inhibits the ventrolateral thalamus. This leads in turn to decreased inhibition of (and ultimately decreased control over) the motor cortex. The subthalamic nucleus appears to increase its activity in Parkinson's Disease as well, and this is believed to contribute to the symptoms of the disease.

Essential Tremor (ET), a.k.a., Benign Essential Tremor, is the most common movement disorder. It is a syndrome characterized by a slowly progressive postural and/or kinetic tremor, usually affecting both upper extremities. The prevalence of ET in the US is estimated at 0.3–5.6% of the general population. A 45-year study of ET in Rochester, Minn. reported an age- and gender-adjusted prevalence of 305.6 per 100,000 and an incidence of incidence of 23.7 per 100,000.

ET affects both sexes equally. The prevalence of ET increases with age. There are bimodal peaks of onset—one in late adolescence to early adulthood and a second peak in older adulthood. The mean age at presentation is 35–45 years. ET usually presents by 65 years of age and virtually always by 70 years. Tremor amplitude slowly increases over time. Tremor frequency decreases with increasing age. An 8–12 Hz tremor is seen in young adults and a 6–8 Hz tremor is seen in the elderly. Although ET is progressive, no association has been found between age of onset and severity of disability.

Mortality rates are not increased in ET. However, disability from ET is common. Significant changes in livelihood and socializing are reported by 85% of individuals with ET, and 15% report being seriously disabled due to ET. Decreased quality of life results from both loss of function and embarrassment. In a study of hereditary ET, 60% did not seek employment; 25% changed jobs or took early retirement; 65% did not dine out; 30% did not attend parties, shop alone, partake of a favorite hobby or sport, or use public transportation; and 20% stopped driving.

A number of US patents have addressed using electrical and/or drug stimulation to increase and/or decrease excitement of various brain structures to treat movement disorders. See, for instance, U.S. Pat. Nos. 6,094,598; 5,833,709; 5,716,377; 5,832,932; 5,711,316; 5,792,186; and 6,227,203. Portions of these seven patents are identical, and they teach both increasing excitement/activity (or decreasing inhibition) and decreasing excitement/activity (or increasing inhibition) of the ventrolateral (VL) thalamus, the globus pallidus interna (GPi), the substantia nigra reticulata (SNr), the subthalamic nucleus (STN), the globus pallidus externa (GPe), the neostriatum, and the striatum. Also taught is increasing excitement of the motor cortex, stiatopallidal fiber pathway, GPe to STN fiber pathway, pallido-thalamic axons, putamen to GPe fibers, and subthalamo-pallidal tracts. U.S. Pat. No. 6,356,784 teaches increasing the activity of the pendunolopontine nucleus (PPN) to treat movement disorders such as Parkinson's Disease, while decreasing PPN activity is used for treating other conditions such as schizophrenia.

While these various treatment locations, methods, and systems exist, the inventors believe that enhanced systems, alternative locations, and modified methods will lead to improved treatment of movement disorders.

BRIEF SUMMARY OF THE INVENTION

The invention disclosed and claimed herein provides systems and methods for introducing one or more stimulating drugs and/or applying electrical stimulation to one or more areas of the brain for treating or preventing movement disorders, as well as the symptoms and pathological consequences thereof. Treatment locations include the nucleus tractus solitarius (NTS), pallidosubthalamic tracts, and putamen to GPi fibers. In addition, treatment by decreasing activity of pallido-thalamic axons, putamen to GPe fibers, and/or subthalamo-pallidal fibers is taught.

The treatment provided by the invention may be carried out by one or more system control units (SCUs) that apply electrical stimulation and/or one or more stimulating drugs to one or more predetermined stimulation sites in the brain. In some forms of an SCU, one or more electrodes are surgically implanted to provide electrical stimulation from an implantable signal/pulse generator (IPG) and/or one or more infusion outlets and/or catheters are surgically implanted to infuse drug(s) from an implantable pump. In other forms of an SCU, a miniature implantable neurostimulator (a.k.a., a microstimulator), such as a Bionic Neuron (also referred to as a BION® microstimulator), is implanted. The systems of the invention may also include one or more sensors for sensing symptoms or conditions that may indicate a needed treatment.

In some configurations, the SCU is implanted in a surgically-created shallow depression or opening in the skull, such as in the temporal, parietal, or frontal bone. In some such configurations, one or more electrode leads and/or catheters attached to the SCU run subcutaneously to an opening in the skull and pass through the opening into or onto the brain parenchyma and surrounding tissue. The SCUs programmed to produce electrical stimulation may provide either monopolar electrical stimulation, e.g., using the SCU case as an indifferent electrode, or bipolar electrical stimulation, e.g., using one of the electrodes of an electrode array as an indifferent electrode.

The SCU used with the present invention possesses one or more of the following properties, among other properties:

- at least one electrode for applying stimulating current to surrounding tissue and/or a pump and at least one outlet for delivering a drug or drugs to surrounding tissue;
- electronic and/or mechanical components encapsulated in a hermetic package made from biocompatible material(s);
- an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;
- means for receiving and/or transmitting signals via telemetry;
- means for receiving and/or storing electrical power within the SCU; and
- a form factor making the SCU implantable in a depression or opening in the skull and/or in the brain.

An SCU may operate independently, or in a coordinated manner with other implanted SCUs, other implanted devices, and/or with devices external to a patient's body. For instance, an SCU may incorporate means for sensing a patient's condition. Sensed information may be used to control the electrical and/or drug stimulation parameters of the SCU in a closed loop manner. The sensing and stimulating means may be incorporated into a single SCU, or a sensing means may communicate sensed information to at least one SCU with stimulating means.

BRIEF DESCRIPTION OF THE DRAWINGS

The above and other aspects of the present invention will be more apparent from the following more particular description thereof, presented in conjunction with the following drawings wherein:

FIGS. 1B and 1C are section views through the brain stem depicted in FIG. 1A;

FIG. 2A depicts the medial surface of the brain;

FIGS. 3A, 3B, and 3C show some possible configurations of an implantable microstimulator of the present invention;

Corresponding reference characters indicate corresponding components throughout the several views of the drawings.

DETAILED DESCRIPTION OF THE INVENTION

Figure 1A:
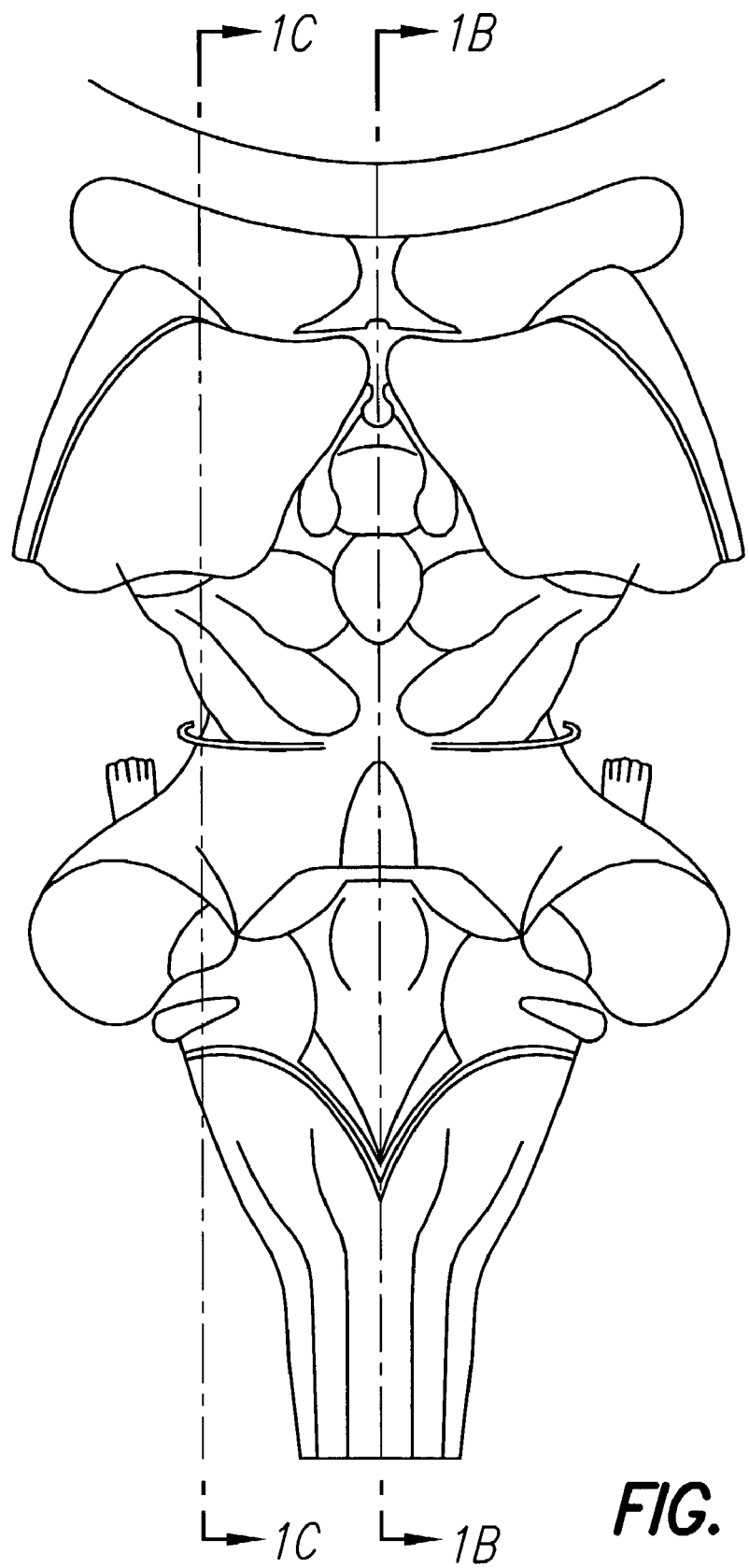
FIG. 1A depicts the dorsal surface of the brain stem.

The following description is of the best mode presently contemplated for carrying out the invention. This description is not to be taken in a limiting sense, but is made merely for the purpose of describing the general principles of the invention. The scope of the invention should be determined with reference to the claims.

The pathophysiology of essential tremor (ET) is essentially unknown. There are no known pathological findings associated with ET. However, the following has been hypothesized: 1) ET is the result of an abnormally functioning central oscillator, which is located in Guillain Mollaret triangle near the brainstem, and involves the inferior olivary nucleus. 2) There is probable involvement of cerebellar-brainstem-thalamic-cortical circuits.

When harmaline, a Monoamine Oxidase (MAO) inhibitor, is administered to primates with lesions of ventromedial tegmental tract or lateral cerebellum, an ET-like tremor is produced. In these animals, inferior olivary nucleus neurons file synchronously at the tremor frequency. C-2-deoxyglucose PET studies demonstrate hypermetabolism in the inferior olivary nuclei of rats and cats with harmaline-induced tremor. Stimulation of the vagus nerve helped resolve tremor in rats with harmaline-induced tremor.

In patients with ET, [$^{18}$F]-fluorodeoxyglucose PET studies identified increased glucose consumption in the medulla. [$^{15}$O]-H$_2$O PET studies demonstrate an increase in medullary regional cerebral blood flow (CBF) in subjects with ET, only after the administration of ethanol, and showed bilateral overactivity of cerebellar circuitry.

The nucleus tractus solitarius (NTS) sends fibers bilaterally to the reticular formation and hypothalamus that are important in the reflex control of cardiovascular, respiratory, and gastrointestinal functions. The NTS also provides input to the dorsal motor nucleus of the vagus that enables the parasympathetic fibers of the vagus nerve to control these reflex responses. The NTS runs the entire length of the medulla oblongata, and the NTS receives somatic sensory input from all cranial nerves, with much of its input coming from the vagus nerve. Since the NTS receives much of its input from the vagus nerve, and since electrical stimulation of the vagus nerve has been demonstrated to be effective in the treatment of an animal model of essential tremor (i.e., for harmaline-induced tremor), then electrical stimulation of the NTS may be effective in the treatment of movement disorders such as essential tremor.

Patients suffering from tremor and other symptoms may undergo surgery to lesion a part of the brain (e.g., the ventral intermediate (Vim) nucleus of the thalamus the internal segment of the globus pallidus (GPi), or the subthalamic nucleus (STN)), which may afford some relief. However, a lesion is irreversible, and may lead to side effects such as dysarthria or cognitive disturbances. Additionally, lesions generally yield effects on only one side of the body (the contra-lateral side), and bilateral lesions are significantly more likely to produce side effects. Other surgical procedures, such as fetal tissue transplants, are costly and unproven.

Other areas of the brain exhibit decreased neural activity in some patients with movement disorders. For instance, some Parkinson's disease patients demonstrate decreased neural activity in parts of the caudate and putamen, the external segment of the globus pallidus (GPe), substantia nigra, and/or parts of the thalamus.

An article published online by Gill, et al. describes delivery of glial cell line-derived neurotrophic factor (GDNF) directly into the putamen of five Parkinson patents in a phase 1 safety trial. [See Gill, et al. "Direct brain infusion of glial cell line-derived neurotrophic factor In Parkinson disease." *Nature Medicine* epub ahead of print: 2003 Mar. 31.] Baseline positron emission tomography (PET) scans indicated that the posterior segment of the putamen in all patients had low [$^{18}$F]dopa uptake. After 18 months, PET scans showed a 28% increase in putamen dopamine storage, in contrast to the predicted decline of up to 20% over this period for Parkinson disease patients. The authors note, however, that the exact mechanism by which GDNF works has yet to be established.

Levy, et al., 2001, present data based on microelectrode recordings from the GPi and the STN during administration of apomorphine, a fast-acting non-selective $D_1$-dopamine and $D_2$-dopamine receptor agonist. [See Levy, et al. "Effects of apomorphine on subthalamic nucleus and globus pallidus internus neurons in patients with Parkinson's disease." *Journal of Neurophysiology* 2001 July;86(1):249–60.] Apomorphine has previously been demonstrated to ameliorate symptoms of Parkinson's disease. In the study, the authors administered doses of apomorphine sufficient to produce relief of Parkinson symptoms, but not sufficient to induce common side effects such as dyskinetic movements. Following baseline microelectrode recordings, apomorphine was administered. The spontaneous discharge of neurons encountered before, during, and after the effect of apomorphine had waned was also sampled.

A reduction in Parkinson symptoms (e.g., limb tremor) was observed in patients when apomorphine reached therapeutic levels. Apomorphine significantly decreased the overall firing rates of GPi neurons, but there was no change in the overall firing rate of neurons in the STN. Concurrent with a reduction in limb tremor, the percentage of cells with tremor-related activity (i.e., tremor cells) was found to be significantly reduced from 19% to 6% in the STN and from 14% to 0% in the GPi following apomorphine administration. Apomorphine also decreased the firing rate of STN tremor cells. As the effects of apomorphine waned, the overall firing rates of GPi neurons increased. In contrast to the findings above, Stefani, et al., 2002, found that administration of apomorphine did indeed reduce the firing rates of all STN cells in patients with Parkinson's disease, concurrent with a reduction in the clinical symptoms of Parkinson's disease. [See Sefani, et al., "Subdyskinetic apomorphine responses in globus pallidus and subthalamus of parkinsonian patients: lack of clear evidence for the 'indirect pathway'." *Clinical Neurophysiology* 2002 January;113(1): 91–100.] These results suggest that the discharge frequency of the GPi and possibly of the STN is a measurable quantity that correlates with the clinical efficacy of medication.

While not previously observed, this GPi discharge frequency phenomenon may occur during deep brain stimulation (DBS) as well. The subthalamic nucleus (STN) is believed to demonstrate increased neurotransmitter release in Parkinson's disease, and it responds to deep brain stimulation. Thus, it may demonstrate a similar discharge frequency phenomenon as the GPi. Since the Vim nucleus of the thalamus also responds to deep brain stimulation, it may also demonstrate a similar discharge frequency phenomenon.

In addition, high frequency chronic electrical stimulation (i.e., frequencies above 100 Hz) of certain areas of the brain has been demonstrated to be as efficacious as producing a lesion in any one of those areas. In contrast to ablation surgery, chronic electrical stimulation is reversible. Additionally, stimulation parameters may be adjusted to minimize side effects while maintaining efficacy; such "fine tuning" is unavailable when producing a lesion.

An implantable chronic stimulation device for DBS is available and similar systems are under development. DBS has proven to be effective for treating some patients with movement disorders; however, the current procedure is highly invasive, and the initial surgery for placement of the available system requires essentially an entire day. These systems require the power source and stimulation electronics to be implanted far from the electrodes, generally in the chest or elsewhere in the trunk of the body. These bulky systems therefore require extensive invasive surgery for implantation, and breakage of the long leads is highly likely. In addition, current DBS systems for movement disorders use no feedback for regulation of stimulation.

For instance, the system manufactured by Medtronic, Inc. of Minneapolis, Minn. has several problems that make it an unacceptable option for some patients. It requires a significant surgical procedure for implantation, as the implantable pulse generator (IPG), a major component of the system containing the stimulation electronics and power source, is implanted in the thorax and connected via a subcutaneous tunnel to an electrode through the chest, neck and head into the brain. Additionally, the IPG is bulky, which may produce an unsightly bulge at the implant site (e.g., the chest), especially for thin patients.

Figure 1B:
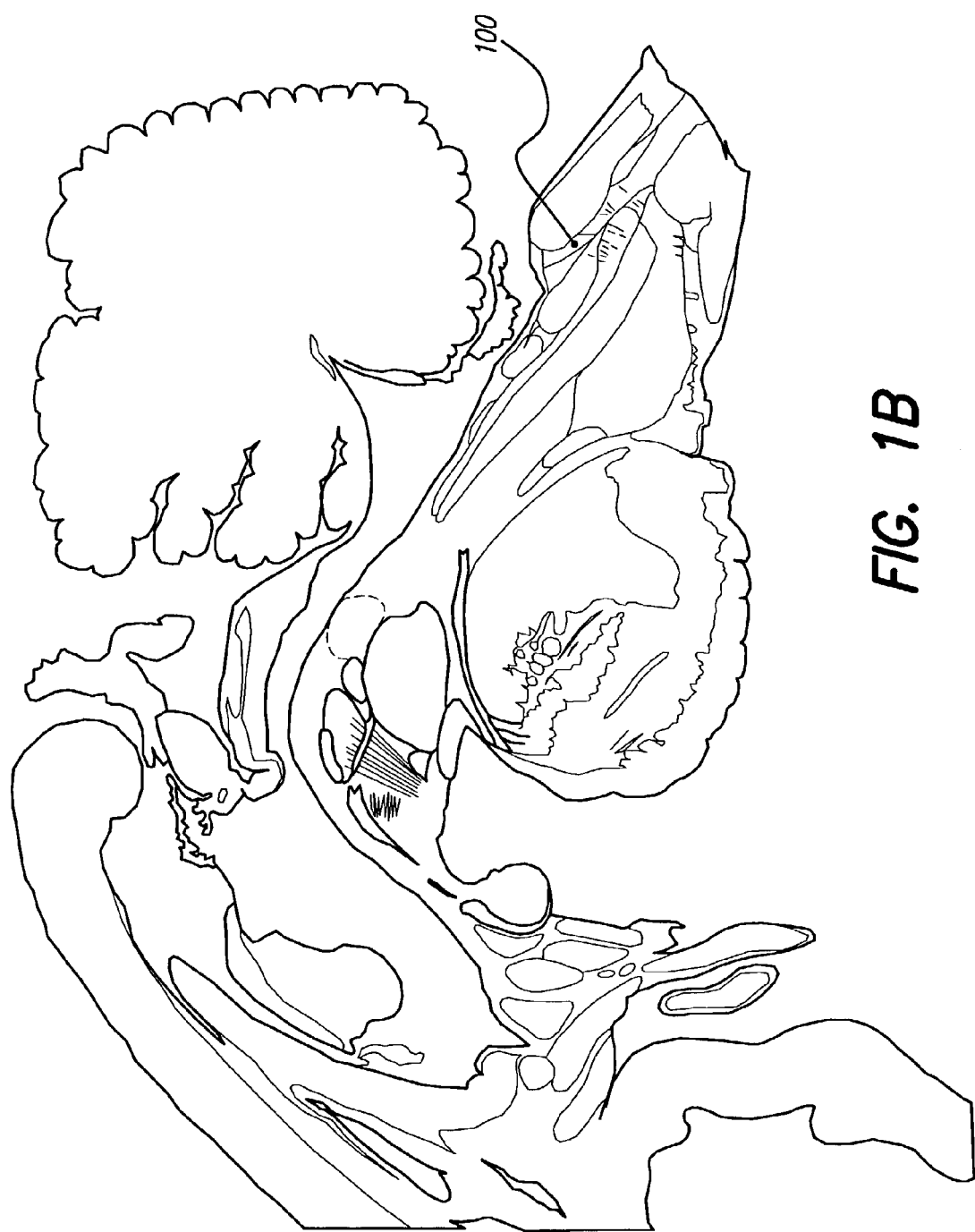
Figure 2B:
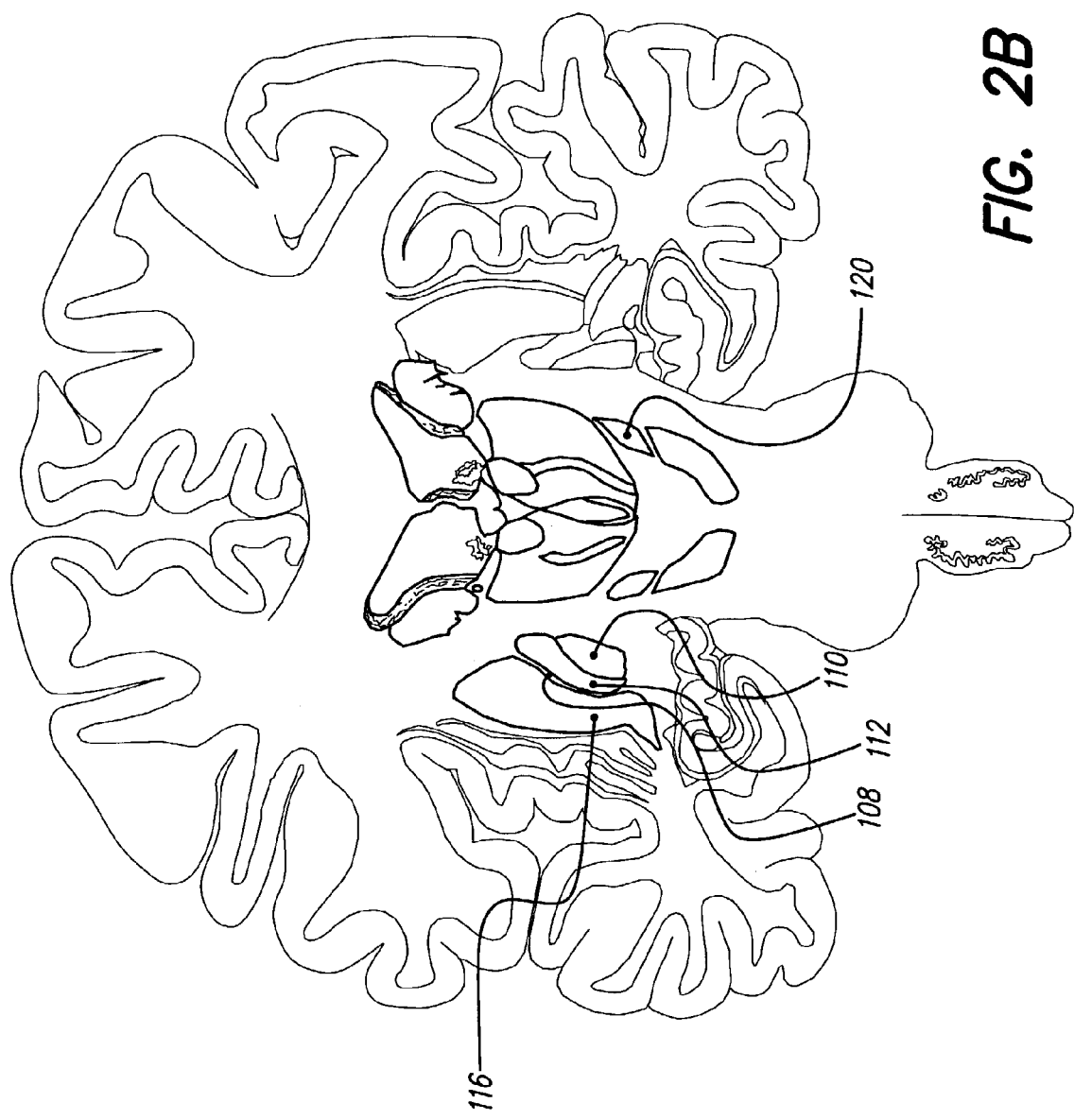
FIG. 2B is a coronal section view of the brain of FIG. 2A.

FIG. 1A depicts the dorsal surface of the brain stem, and FIGS. 1B and 1C are section views through the brain stem depicted in FIG. 1A, while FIG. 2A depicts the medial surface of the brain and FIG. 2B is a coronal section view of the brain of FIG. 2A. FIG. 1B shows the location of the nucleus tractus solitarius (NTS) 100. FIG. 1C shows the locations of the substantia nigra pars reticulata 102 (as seen in the figure, the substantia nigra pars reticulata is included in the substantia nigra, as is the substantia nigra pars compacta), the ventral intermediate (Vim) thalamic nucleus 104, the pallidosubthalamic tracts 106, and the pallido-thalamic axons 107 (as seen in the figure, pallido-thalamic axons are found in the lenticular fasciculus and the ansa lenticularis). FIG. 2B shows the location of the putamen to GPe fibers 108. FIGS. 1C and 2B show the locations of the internal globus pallidus (GPi) 110, the external globus pallidus (GPe) 112, the putamen 116, and the subthalamic nucleus (STN) 120.

The present invention provides electrical and/or drug stimulation to one or more of the above mentioned areas (and in particular, the NTS 100, pallidosubthalamic tracts 106, the pallido-thalamic axons 107, the putamen to GPe fibers 108), subthalamo-pallidal fibers (not shown), putamen to GPi fibers (not shown), and/or the cerebellum (not shown) as a treatment for movement disorders. Thus, via mechanisms described in more detail herein, the present invention provides electrical stimulation and/or stimulating drugs to these areas to adjust the level of neural activity in these areas, and thereby treat or prevent motor disorders.

For instance, for patients who demonstrate increased neural activity of Vim 104, pallido-thalamic axons 107, putamen to GPe fibers 108, GPi 110, STN 120, subthalamo-pallidal fibers, and/or the cerebellum, inhibitory stimulation may be applied to one or more of these areas. On the other hand, for patients who exhibit decreased neural activity of NTS 100, substantia nigra pars reticulata 102, pallido-subthalamic tracts 106, GPe 112, putamen 116, and/or putamen to GPi fibers, excitatory stimulation may be applied to one or more of these areas. As used herein, stimulate, stimulation, and stimulating refer to infusion of a stimulating drug(s) and/or supplying electrical current pulses. As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

Herein, stimulating drugs comprise medications and other pharmaceutical compounds, anesthetic agents, synthetic or natural hormones, neurotransmitters, interleukins, cytokines, lymphokines, chemokines, growth factors (e.g., glial cell line-derived neurotrophic factor (GDNF), brain cell line-derived neurotrophic factor (BDNF)), and other intracellular and intercellular chemical signals and messengers, and the like. Certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein may include stimulation of cell bodies and axons in the area.

A number of drugs have demonstrated efficacy in the treatment of Parkinson's disease. Primary among these is levodopa. Levodopa is effective for Parkinson's disease only in the brain; in the periphery it can cause side effects. Levodopa is typically administered with a dopa decarboxylase inhibitor in order to prevent systemic side effects.

Patent Cooperation Treaty publication WO 00/38669(A2) teaches administration of naloxone to the substantia nigra for the prevention of neural degeneration. (Naloxone is an opiate antagonist.) Since degeneration of the substantia nigra is the primary pathology of Parkinson's disease, chronic administration of naloxone to the substantia nigra may be therapeutic.

In some alternatives, stimulation is provided by at least one system control unit (SCU) that is an implantable signal generator connected to an electrode(s) and/or an implantable pump connected to a catheter(s). These systems deliver electrical stimulation and/or one or more stimulating drugs to specific areas in the brain. One or more electrodes are surgically implanted in the brain to provide electrical stimulation, and/or one or more catheters are implanted in the brain to infuse the stimulating drug(s).

In various alternatives, stimulation is provided by one or more SCUs that are small, implantable stimulators, referred to herein as microstimulators. The microstimulators of the present invention may be similar to or of the type referred to as BION® devices (see FIGS. 3A, 3B, and 3C). The following documents describe various details associated with the manufacture, operation and use of BION implantable microstimulators, and are all incorporated herein by reference:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| PCT Publication WO 98/37926 | Published Sep. 3, 1998 | Battery-Powered Patient Implantable Device |
| PCT Publication WO 98/43700 | Published Oct. 8, 1998 | System of Implantable Devices For Monitoring and/or Affecting Body Parameters |
| PCT Publication WO 98/43701 | Published Oct. 8, 1998 | System of Implantable Devices For Monitoring and/or Affecting Body Parameters |
| U.S. Pat. No. 6,051,017 | Issued Apr. 18, 2000 | Improved Implantable Microstimulator and Systems Employing Same |
| | Published September 1997 | Micromodular Implants to Provide Electrical Stimulation of Paralyzed Muscles and Limbs, by Cameron, et al., published in IEEE Transactions on Biomedical Engineering, Vol. 44, No. 9, pages 781–790. |

Figure 3B:
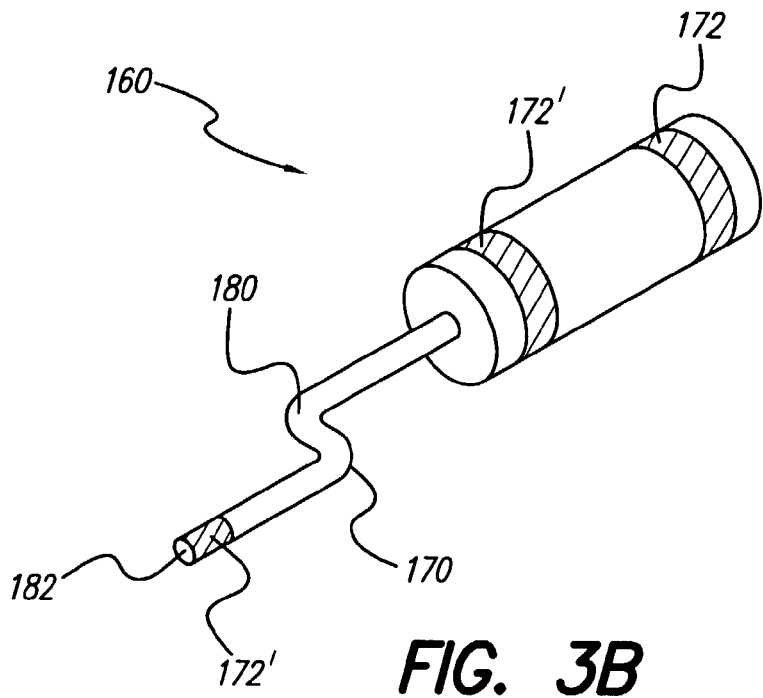
Figure 3C:
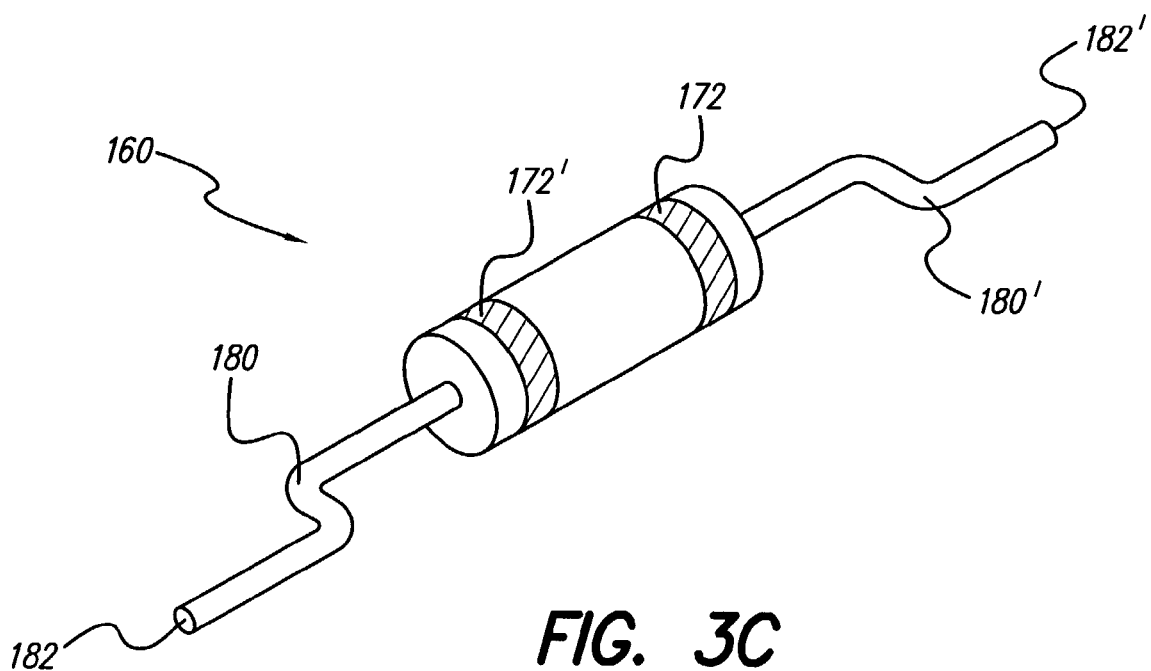

As shown in FIGS. 3A, 3B, and 3C, microstimulator SCUs 160 may include a narrow, elongated capsule 152 containing electronic circuitry 154 connected to electrodes 172 and 172', which may pass through the walls of the capsule at either end. Alternatively, electrodes 172 and/or 172' may be built into the case and/or arranged on a catheter 180 (FIG. 3B) or at the end of a lead, as described below. As detailed in the referenced publications, electrodes 172 and 172' generally comprise a stimulating electrode (to be placed close to the target) and an indifferent electrode (for completing the circuit). Other configurations of microstimulator SCU 160 are possible, as is evident from the above-referenced publications, and as described in more detail herein.

Certain configurations of implantable microstimulator SCU 160 are sufficiently small to permit placement in or adjacent to the structures to be stimulated. For instance, in these configurations, capsule 152 may have a diameter of about 4–5 mm, or only about 3 mm, or even less than about 3 mm. In these configurations, capsule length may be about 25–35 mm, or only about 20–25 mm, or even less than about 20 mm. The shape of the microstimulator may be determined by the structure of the desired target, the surrounding area, and the method of implantation. A thin, elongated cylinder with electrodes at the ends, as shown in FIGS. 3A, 3B, and 3C, is one possible configuration, but other shapes, such as cylinders, disks, spheres, and helical structures, are possible, as are additional electrodes, infusion outlets, leads, and/or catheters.

Microstimulator SCU 160, when certain configurations are used, may be implanted with a surgical tool such as a tool specially designed for the purpose, or with a hypodermic needle, or the like. Alternatively, microstimulator SCU 160 may be implanted via conventional surgical methods (e.g., via a small incision), or may be placed using endoscopic or laparoscopic techniques. A more complicated surgical procedure may be required for sufficient access to, for instance, the NTS 100, or for fixing the microstimulator in place.

Deep brain stimulation (DBS) electrodes are typically targeted and implanted with the guidance of a stereotactic frame. The diameter of the test or stimulation DBS electrodes is typically 1.5 mm or less. Microstimulator SCU 160 may be implanted with the aid of a stereotactic frame/tools via a minimal surgical procedure (e.g., through a small burr hole) adjacent to or in the sites mentioned above for the treatment of movement disorders, e.g., the NTS, among other locations. As mentioned earlier, microstimulator SCU 160 may have a diameter of about 3 mm or less, allowing it to fit through a conventional burr hole in the skull. Instead of or in addition to stereotactic techniques, microstimulator SCU 160 may be implanted with the aid of other techniques, e.g., CT or ultrasound image guidance. However, even with such techniques, microstimulator SCU 160 itself requires only a relatively small hole in the skull for implantation, i.e., a hole as large as the diameter of the implanted device.

The external surfaces of microstimulator SCU 160 may advantageously be composed of biocompatible materials. Capsule 152 may be made of, for instance, glass, ceramic, or other material that provides a hermetic package that will exclude water vapor but permit passage of electromagnetic fields used to transmit data and/or power. Electrodes 172 and 172' may be made of a noble or refractory metal or compound, such as platinum, iridium, tantalum, titanium, titanium nitride, niobium or alloys of any of these, in order to avoid corrosion or electrolysis which could damage the surrounding tissues and the device.

In certain embodiments of the instant invention, microstimulator SCU 160 comprises two, leadless electrodes. However, either or both electrodes 172 and 172' may alternatively be located at the ends of short, flexible leads as described in U.S. patent application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of microstimulator SCU 160, while allowing most elements of the microstimulator to be located in a more surgically convenient site. This minimizes the distance traversed and the surgical planes crossed by the device and any lead(s). In most uses of this invention, the leads are no longer than about 150 mm.

As mentioned earlier, stimulation is provided in accordance with the teachings of the present invention by electrical stimulation and/or one or more stimulating drugs delivered to the body by one or more system control units (SCUs). In the case of electrical stimulation only, SCUs include a microstimulator and/or an implantable pulse/signal generator (IPG), or the like. In the case of drug infusion only, an SCU comprises an implantable pump or the like. In cases requiring both electrical stimulation and drug infusion, more than one SCU may be used. Alternatively, when needed and/or desired, an SCU provides both electrical stimulation and one or more stimulating drugs.

Figure 4:
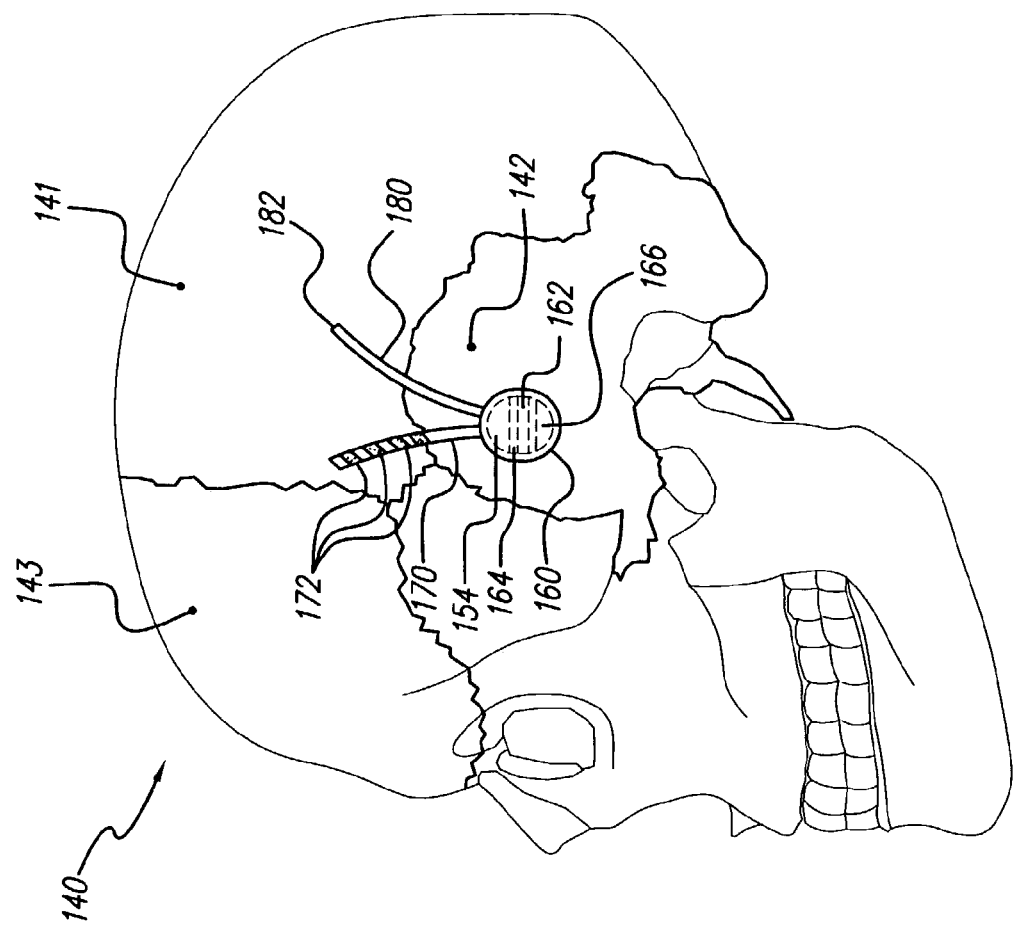
FIG. 4 illustrates a lateral view of the skull and components of some embodiments of the invention.

As depicted in FIG. 4, some embodiments of SCU 160 may be (but are not necessarily) implanted beneath the scalp, such as in a surgically-created shallow depression or opening in the skull 140, for instance, in parietal bone 141, temporal bone 142, or frontal bone 143. In several embodiments, SCU 160 conforms to the profile of surrounding tissue(s) and/or bone(s), and is small and compact. This may minimize pressure applied to the skin or scalp, which pressure may result in skin erosion or infection. In various embodiments, SCU 160 has a diameter of about 75 mm, or only about 65 mm, or even less than about 55 mm. In these configurations, SCU thickness may be approximately 10–12 mm, or even less than about 10 mm.

Figure 5:
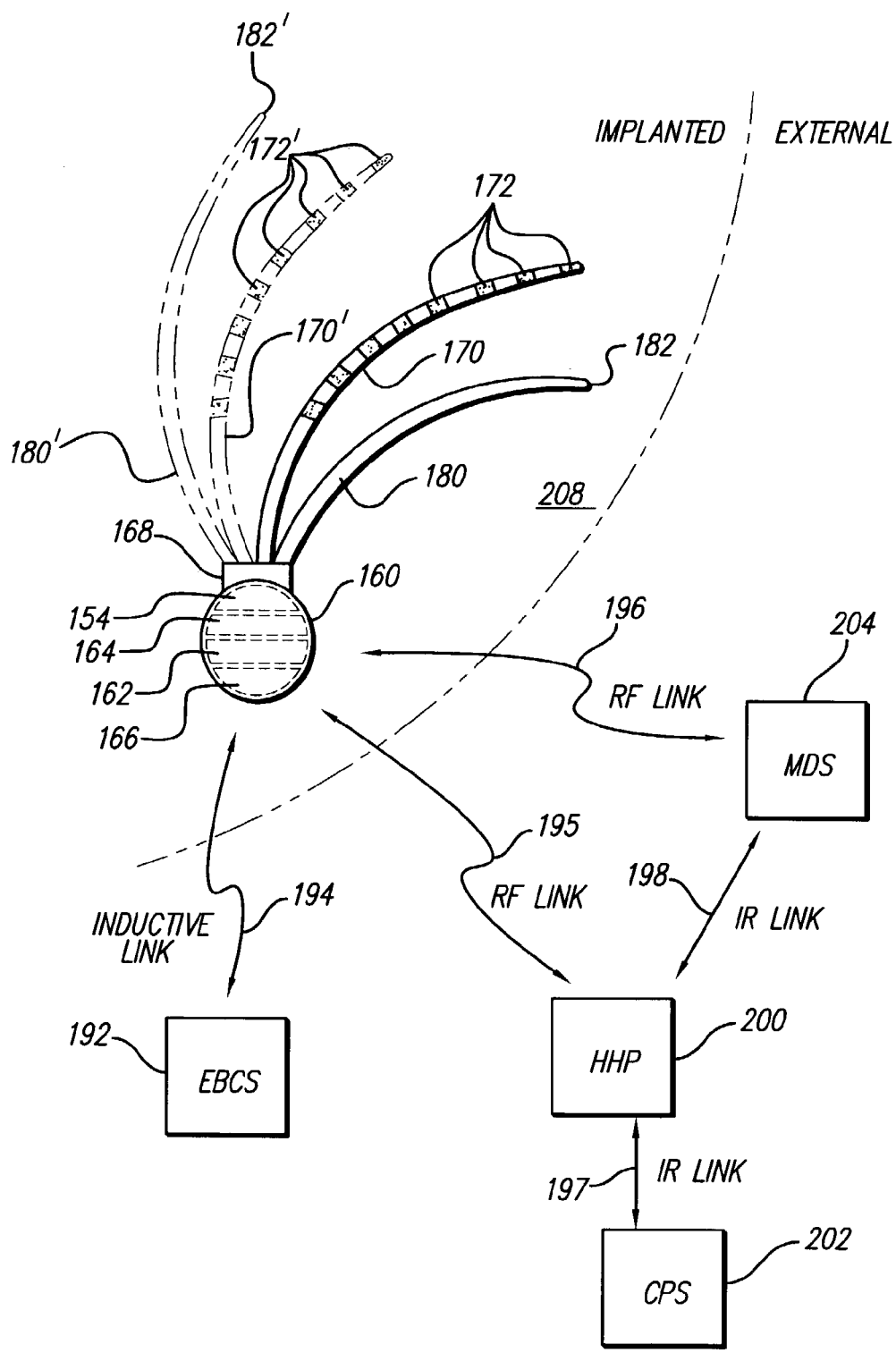
FIG. 5 illustrates internal and external components of certain embodiments of the invention.

As seen in the embodiments depicted in FIG. 5, one or more electrode leads 170 and/or catheters 180 attached to SCU 160 run subcutaneously, for instance, in a surgically-created shallow groove(s) in the skull, to an opening(s) in the skull, and pass through the opening(s) into or onto the brain parenchyma and surrounding tissue. Recessed placement of the SCU and the lead(s) and/or catheter(s) may decrease the likelihood of erosion of the overlying skin, and may minimize any cosmetic impact.

In embodiments such as in FIG. 5, electrode(s) 172 are carried on lead 170 having a proximal end coupled to SCU 160. The lead contains insulated wires electrically connecting electrodes 172 to SCU 160. SCU 160 contains electrical components 154 that produce electrical stimulation pulses that travel through the wires of lead 170 and are delivered to electrodes 172, and thus to the tissue surrounding electrodes 172. To protect the electrical components inside SCU 160, some or all of the case of the SCU may be hermetically sealed. For additional protection against, e.g., impact, the case may be made of metal (e.g. titanium) or ceramic, which materials are also, advantageously, biocompatible. In addition, SCU 160 may be configured to be Magnetic Resonance Imaging (MRI) compatible.

In some alternatives, the electrical stimulation may be provided as described in International Patent Application Serial Number PCT/US01/04417 (the '417 application), filed Feb. 12, 2001, and published Aug. 23, 2001 as WO 01/60450, which application is incorporated herein by reference in its entirety. As such, the electrical stimulation of the present invention may be as provided in this PCT application, which is directed to a "Deep Brain Stimulation System for the Treatment of Parkinson's Disease or Other Disorders".

In the case of treatment alternatively or additionally constituting drug infusion, SCU 160 (which herein refers to IPGs, implantable pumps, IPG/pump combinations, microstimulators for drug and/or electrical stimulation, and/or other alternative devices described herein) may contain at least one pump 162 for storing and dispensing one or more drugs through outlet(s) 182/182' and/or catheter(s) 180/180' into a predetermined site(s) in the brain tissue. When a catheter is used, it includes at least one infusion outlet 182, usually positioned at least at a distal end, while a proximal end of the catheter is connected to SCU 160.

According to some embodiments of the invention, such as described in the previously referenced '417 application and as depicted in FIG. 5, at least one lead 170 is attached to SCU 160, via a suitable connector 168, if necessary. Each lead includes at least one electrode 172, and may include as many as sixteen or more electrodes 172. Additional leads 170' and/or catheter(s) 180' may be attached to SCU 160. Hence, FIG. 5 shows (in phantom lines) a second catheter 180', and a second lead 170', having electrodes 172' thereon, also attached to SCU 160. Similarly, the SCUs 160 of FIGS. 3A, 3B, and 3C have outlets 182, 182' for infusing a stimulating drug(s) and electrodes 172, 172' for applying electrical stimulation.

Substantially cylindrical catheter(s) 180 and lead(s) 170 of certain embodiments of the present invention may be less than about 5 mm in diameter, or even less than about 1.5 mm in diameter. In embodiments using one or more paddle-shaped leads (e.g., cerebellum stimulation may use substantially cylindrical or paddle-shaped leads), lead(s) 170 may be less than 15 mm in width, and less than 1.5 mm in thickness. Electrodes 172, 172' on leads 170, 170' may be arranged as an array, for instance, as two or more collinear electrodes, or even as four or more collinear electrodes, or they may not be collinear. A tip electrode may also be supplied at the distal end of one or more leads.

In some embodiments, SCU 160 is programmable to produce either monopolar electrical stimulation, e.g., using the SCU case as an indifferent electrode, or bipolar electrical stimulation, e.g., using one of the electrodes of the electrode array as an indifferent electrode. Some embodiments of SCU 160 have at least four channels and drive up to sixteen electrodes or more.

SCU 160 contains, when necessary and/or desired, electronic circuitry 154 for receiving data and/or power from outside the body by inductive, radio frequency (RF), or other electromagnetic coupling. In some embodiments, electronic circuitry 154 includes an inductive coil for receiving and transmitting RF data and/or power, an integrated circuit (IC) chip for decoding and storing stimulation parameters and generating stimulation pulses (either intermittent or continuous), and additional discrete electronic components required to complete the electronic circuit functions, e.g. capacitor(s), resistor(s), coil(s), and the like.

SCU 160 also includes, when necessary and/or desired, a programmable memory 164 for storing a set(s) of data, stimulation, and control parameters. Among other things, memory 164 may allow electrical and/or drug stimulation to be adjusted to settings that are safe and efficacious with minimal discomfort for each individual. Specific parameters may provide therapeutic advantages for various types and severities of movement disorders. For instance, some patients may respond favorably to intermittent stimulation, while others may require continuous treatment for relief. In some embodiments, electrical and drug stimulation parameters are controlled independently, e.g., continuous electrical stimulation and no drug stimulation. However, in some instances, they may advantageously be coupled, e.g., electrical stimulation may be programmed to occur only during drug infusion.

In addition, different stimulation parameters may have different effects on neural tissue. Therefore, parameters may be chosen to target specific neural populations and/or to exclude others, or to increase neural activity in specific neural populations and/or to decrease neural activity in others. For example, relatively low levels of stimulation current (e.g., about 0.5 mA to about 5.0 mA, or even about 0.05 mA to about 2.0 mA) are likely to recruit only relatively large diameter fibers. According to certain embodiments of the invention, the stimulation can selectively increase neural activity of only the relatively large diameter fibers of NTS 100. Relatively low amplitude electrical current pulses are likely to produce such selective excitation.

As another example, relatively low frequency neurostimulation (i.e., less than about 100–150 Hz) typically has an excitatory effect on surrounding neural tissue, leading to increased neural activity, whereas relatively high frequency neurostimulation (i.e., greater than about 100–150 Hz) may have an inhibitory effect, leading to decreased neural activity. Similarly, excitatory neurotransmitters (e.g., glutamate, dopamine, norepinephrine, epinephrine, acetylcholine, serotonin), agonists thereof (e.g., glutamate receptor agonist(s), apomorphine), and agents that act to increase levels of an excitatory neurotransmitter(s) (e.g., edrophonium, Mestinon) generally have an excitatory effect on neural tissue, while inhibitory neurotransmitters (e.g., dopamine, glycine, and gamma-aminobutyric acid, a.k.a. GABA), agonists thereof (e.g., muscimol, apomorphine), and agents that act to increase levels of an inhibitory neurotransmitter(s) generally have an inhibitory effect. (Dopamine acts as an excitatory neurotransmitter in some locations and circumstances, and as an inhibitory neurotransmitter in other locations and circumstances.) However, antagonists of inhibitory neurotransmitters (e.g., bicuculline) and agents that act to decrease levels of an inhibitory neurotransmitter(s) have been demonstrated to excite neural tissue, leading to increased neural activity. Similarly, excitatory neurotransmitter antagonists (e.g. prazosin, metoprolol, atropine, benztropine) and agents that decrease levels of excitatory neurotransmitter(s) (e.g., acetylcholinesterase, Group II metabotropic glutamate receptor (mGluR) agonists such as DCG-IV) may inhibit neural activity.

Some embodiments of SCU 160 also include a power source and/or power storage device 166. Possible power options for a stimulation device of the present invention, described in more detail below, include but are not limited to an external power source coupled to the stimulation device, e.g., via an RF link, a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

In embodiments such as shown in FIG. 5, SCU 160 includes a rechargeable battery as a power source/storage device 166. The battery is recharged, as required, from an external battery charging system (EBCS) 192, typically through an inductive link 194. In these embodiments, and as explained more fully in the earlier referenced '417 PCT application, SCU 160 includes a processor and other electronic circuitry 154 that allow it to generate stimulation pulses that are applied to a patient 208 through electrodes 172 and/or outlet(s) 182 in accordance with a program and stimulation parameters stored in programmable memory 164. Stimulation pulses of drugs include various types and/or rates of infusion, such as intermittent infusion, infusion at a constant rate, and bolus infusion.

According to certain embodiments of the invention, an SCU operates independently. According to various embodiments of the invention, an SCU operates in a coordinated manner with other SCU(s), other implanted device(s), and/or other device(s) external to the patient's body. For instance, an SCU may control or operate under the control of another implanted SCU(s), other implanted device(s), and/or other device(s) external to the patient's body. An SCU may communicate with other implanted SCUs, other implanted devices, and/or devices external to a patient's body via, e.g., an RF link, an ultrasonic link, a thermal link, and/or an optical link. Specifically, an SCU may communicate with an external remote control (e.g., patient and/or physician programmer) that is capable of sending commands and/or data to an SCU and that may also be capable of receiving commands and/or data from an SCU.

For example, some embodiments of SCU 160 of the present invention may be activated and deactivated, programmed and tested through a hand held programmer (HHP) 200 (which may also be referred to as a patient programmer and may be, but is not necessarily, hand held), a clinician programming system (CPS) 202 (which may also be hand held), and/or a manufacturing and diagnostic system (MDS) 204 (which may also be hand held). HHP 200 may be coupled to SCU 160 via an RF link 195. Similarly, MDS 204 may be coupled to SCU 160 via another RF link 196. In a like manner, CPS 202 may be coupled to HHP 200 via an infra-red link 197; and MDS 204 may be coupled to HHP 200 via another infra-red link 198. Other types of telecommunicative links, other than RF or infra-red may also be used for this purpose. Through these links, CPS 202, for example, may be coupled through HHP 200 to SCU 160 for programming or diagnostic purposes. MDS 204 may also be coupled to SCU 160, either directly through RF link 196, or indirectly through IR link 198, HHP 200, and RF link 195.

Figure 6:
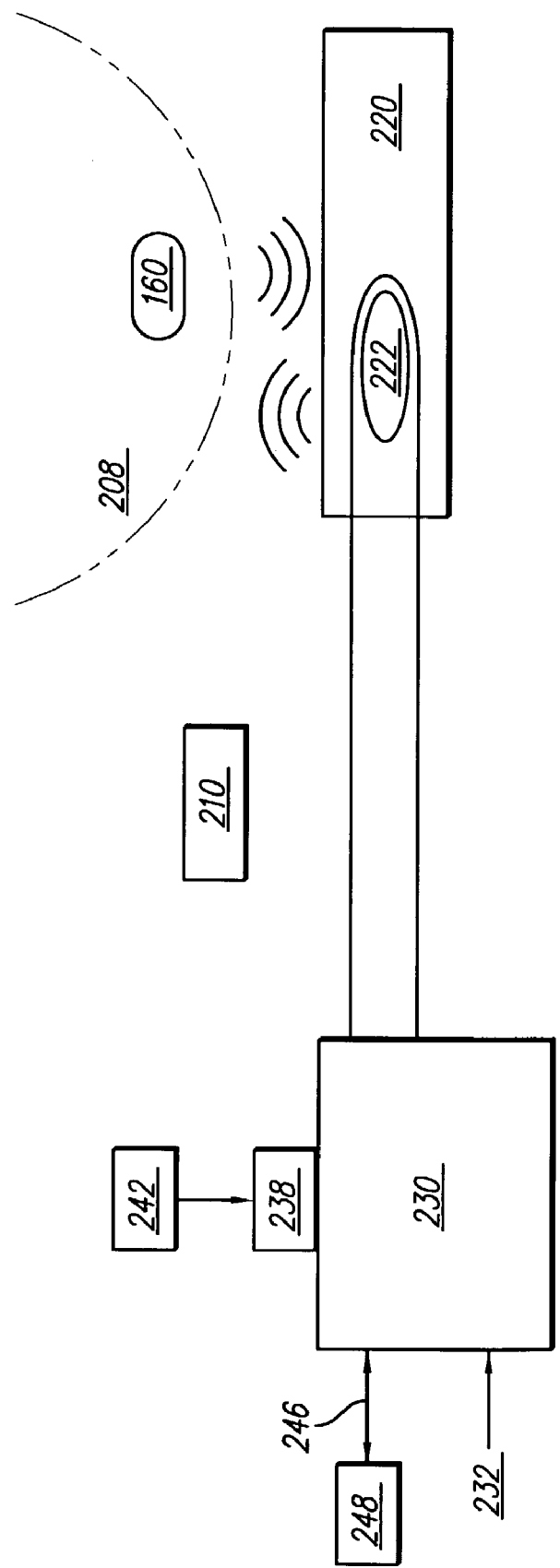
FIG. 6 illustrates external components of various embodiments of the invention.

In certain embodiments, using for example, a BION microstimulator(s) as described in the above referenced publications, and as illustrated in FIG. 6, the patient 208 switches SCU 160 on and off by use of controller 210, which may be handheld. SCU 160 is operated by controller 210 by any of various means, including sensing the proximity of a permanent magnet located in controller 210, sensing RF transmissions from controller 210, or the like.

External components for programming and/or providing power to various embodiments of SCU 160 are also illustrated in FIG. 6. When communication with such an SCU 160 is desired, patient 208 is positioned on or near external appliance 220, which appliance contains one or more inductive coils 222 or other means of communication (e.g., RF transmitter and receiver). External appliance 220 is connected to or is a part of external electronic circuitry appliance 230 which may receive power 232 from a conventional power source. External appliance 230 contains manual input means 238, e.g., a keypad, whereby the patient 208 or a caregiver 242 may request changes in electrical and/or drug stimulation parameters produced during the normal operation of SCU 160. In these embodiments, manual input means 238 includes various electromechanical switches and/or visual display devices that provide the patient and/or caregiver with information about the status and prior programming of SCU 160.

Alternatively or additionally, external electronic appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

The external appliance(s) may be embedded in a cushion, pillow, hat, or the like. Other possibilities exist, including a head band, patch, or other structure(s) that may be affixed to the patient's body or clothing. External appliances may include a package that can be, e.g., worn on the belt, may include an extension to a transmission coil affixed, e.g., with a Velcro® band or an adhesive, or may be combinations of these or other structures able to perform the functions described herein.

In order to help determine the strength and/or duration of electrical stimulation and/or the amount and/or type(s) of stimulating drug(s) required to produce the desired effect, in some embodiments, a patient's response to and/or need for treatment is sensed. For example, head acceleration, electrical activity of the brain (e.g., EEG or discharge frequency of a neural population), nerve activity (e.g., ENG), muscle activity (e.g., limb EMG), or other activity may be sensed.

For instance, one or more electrodes may be used for recording electrical signals from the brain. Recording of the neural activity of one or more areas being stimulated, e.g., NTS 100 or pallido-subthalamic tracts 106, may be performed in order to determine the discharge frequency of the neural population. This sensing may occur during stimulation or during a temporary suspension of stimulation. The amplitude of stimulation is increased if the discharge frequency is above a programmable threshold frequency, and the amplitude of stimulation is decreased if the discharge frequency is less than another programmable threshold frequency. The two programmable threshold frequencies may be the same or may be different in order to achieve hysteresis.

In another example, one or more accelerometers may be used for sensing acceleration of the head. Rhythmic acceleration of the head is seen in head tremor. Thus, the amplitude of rhythmic head acceleration is an indicator of the amplitude of head tremor. The amplitude of stimulation is increased if the amplitude of rhythmic head acceleration is above a programmable threshold amplitude, and the amplitude of stimulation is decreased if the amplitude of rhythmic head acceleration is below a programmable threshold amplitude. The two programmable threshold amplitudes may be the same or may be different in order to achieve hysteresis. This sensing may advantageously be used for patients with significant head tremor as a component of their movement disorder, such as certain patients with benign essential tremor.

Other measures of the state of the patient may additionally or alternatively be sensed. For instance, one or more neurotransmitter levels, their associated breakdown product levels, hormone levels, or other substances, such as dopamine levels, interleukins, cytokines, lymphokines, chemokines, growth factors, electrolytes, enzymes, medication, and/or other drug levels, or levels of any other bloodborne substance(s), and/or changes in one or more of these may be sensed, using, e.g., one or more Chemically Sensitive Field-Effect Transistors (CHEMFETs) such as Enzyme-Selective Field-Effect Transistors (ENFETs) or Ion-Sensitive Field-Effect Transistors (ISFETs, as are available from Sentron CMT of Enschede, The Netherlands). For example, when electrodes of SCU 160 are implanted in or adjacent to pallido-subthalamic tracts 106, a stimulating electrode of SCU 160, or other sensing means contained in the electrode lead, catheter, IPG, microstimulator, or any part of the system may be used to sense changes in neural firing frequency of the pallido-subthalamic tracts 106 resulting from the electrical and/or drug stimulation applied to the pallido-subthalamic tracts 106. (As used herein, "adjacent" or "near" means as close as reasonably possible to targeted tissue, including touching or even being positioned within the tissue, but in general, may be as far as about 150 mm from the target tissue.)

Alternatively, an "SCU" dedicated to sensory processes communicates with an SCU providing stimulation pulses. The implant circuitry 154 may, if necessary, amplify and transmit these sensed signals, which may be digital or analog. Other methods of determining the required electrical and/or drug stimulation include measuring impedance, acidity/alkalinity (via a pH sensor), muscle EMG, head or limb acceleration (e.g., via accelerometer), EEG, ENG, other methods mentioned herein, and others that will be evident to those of skill in the field upon review of the present disclosure. The sensed information may be used to control stimulation parameters in a closed-loop manner.

For instance, in several embodiments of the present invention, a first and second "SCU" are provided. The second "SCU" periodically (e.g. once per minute) records firing rate of neurons in GPi 110 (or the level of a substance, e.g., dopamine or L-Dopa, or an amount of electrical activity, etc.), which it transmits to the first SCU. The first SCU uses the sensed information to adjust electrical and/or drug stimulation parameters according to an algorithm programmed, e.g., by a physician. For example, the amplitude and/or frequency of electrical stimulation may be increased in response to increased firing rate of neurons in GPi 110. In some alternatives, one SCU performs both the sensing and stimulating functions, as discussed in more detail presently.

While an SCU 160 may also incorporate means of sensing symptoms or other prognostic or diagnostic indicators of movement disorders, e.g., via sensing of tremor (e.g., via accelerometer), sensing of dopamine or dopamine agonist levels (e.g., L-dopa), and/or sensing of neural electrical activity (e.g., firing rate of neurons in pallido-subthalamic tracts 106), it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted SCU(s) 160. However, in some cases, it may not be necessary or desired to include a sensing function or device, in which case stimulation parameters are determined and refined, for instance, by patient feedback, or the like.

Thus, it is seen that in accordance with the present invention, one or more external appliances may be provided to interact with SCU 160, and may be used to accomplish, potentially among other things, one or more of the following functions:

Function 1: If necessary, transmit electrical power from the external electronic appliance 230 via appliance 220 to SCU 160 in order to power the device and/or recharge the power source/storage device 166. External electronic appliance 230 may include an automatic algorithm that adjusts electrical and/or drug stimulation parameters automatically whenever the SCU(s) 160 is/are recharged.

Function 2: Transmit data from the external appliance 230 via the external appliance 220 to SCU 160 in order to change the parameters of electrical and/or drug stimulation used by SCU 160.

Function 3: Transmit sensed data indicating a need for treatment or in response to stimulation from SCU 160 (e.g., EEG, dopamine or dopamine agonist level, other neurotransmitter levels, limb tremor, or other activity) to external appliance 230 via external appliance 220.

Function 4: Transmit data indicating state of the SCU 160 (e.g., battery level, drug level, stimulation parameters, etc.) to external appliance 230 via external appliance 220.

By way of example, a treatment modality for movement disorders, e.g., Parkinson's disease, may be carried out according to the following sequence of procedures:

1. A first SCU 160 is implanted so that its electrodes 172 and/or infusion outlet 182 are located in or on or near pallido-subthalamic tracts 106. If necessary or desired, electrodes 172' and/or infusion outlets 182' may additionally or alternatively be located in or on or near NTS 100 or putamen to GPi fibers.
2. Using Function 2 described above (i.e., transmitting data) of external electronic appliance 230 and external appliance 220, first SCU 160 is commanded to produce a series of excitatory electrical stimulation pulses, possibly with gradually increasing amplitude, and possibly while infusing gradually increasing amounts of an excitatory neurotransmitter, e.g., glutamate, or an inhibitory neurotransmitter antagonist, e.g., biculline.
3. After each stimulation pulse, series of pulses, or at some other predefined interval, any change in, e.g., tremor (sensed, e.g., via accelerometer in limb) resulting from the electrical and/or drug stimulation is sensed, for instance, by one or more electrodes 172, 172' or sensors of a second SCU 160, preferably a microstimulator SCU 160, implanted in or on or near a limb(s). If necessary, these responses are converted to data and telemetered out to external electronic appliance 230 via Function 3.
4. From the response data received at external appliance 230 from second SCU 160, or from other assessment, the stimulus threshold for obtaining a response is determined and is used by a clinician 242 acting directly 238 or by other computing means 248 to transmit the desired electrical and/or drug stimulation parameters to first SCU 160 in accordance with Function 2. Alternatively, the second SCU 160 uses the response data to determine the stimulation parameters and transmits the parameters to first SCU 160. In yet another alternative, the second SCU 160 transmits the response data to first SCU 160, which uses the response data directly to determine the stimulation parameters. Finally, some combination of the above may be used.
5. When patient 208 desires to invoke electrical stimulation and/or drug infusion, patient 208 employs controller 210 to set first SCU 160 in a state where it delivers a prescribed stimulation pattern from a predetermined range of allowable stimulation patterns.
6. To cease electrical and/or drug stimulation, patient 208 employs controller 210 to turn off first SCU 160 and possibly also second SCU 160.
7. Periodically, the patient or caregiver recharges the power source/storage device 166 of first and/or second SCU 160, if necessary, in accordance with Function 1 described above (i.e., transmit electrical power).

In another example, a treatment for movement disorders, e.g., essential tremor, may be carried out according to the following sequence of procedures:

1. An SCU 160 is implanted so that its electrodes 172 and possibly also infusion outlet 182 are located in or on or near NTS 100.
2. Using Function 2 described above (i.e., transmitting data) of external electronic appliance 230 and external appliance 220, first SCU 160 is commanded to produce a series of excitatory electrical stimulation pulses, possibly with gradually increasing amplitude, and possibly while infusing gradually increasing amounts of an excitatory neurotransmitter, e.g., glutamate, or an inhibitory neurotransmitter antagonist, e.g., biculline.
3. After each stimulation pulse, series of pulses, or at some other predefined interval, any change in movement disorder signs and symptoms, e.g., change in neural firing rate in GPi 110, resulting from the electrical and/or drug stimulation is sensed, for instance, by one or more of the electrodes 172 of SCU 160. These responses are converted to data and telemetered out to external electronic appliance 230 via Function 3.
4. From the response data received at external appliance 230 from SCU 160, or from other assessment, the stimulus threshold for obtaining a response is determined and is used by a clinician 242 acting directly 238 or by other computing means 248 to transmit the desired electrical and/or drug stimulation parameters to SCU 160 in accordance with Function 2.

5. When patient 208 desires to invoke electrical stimulation and/or drug infusion, patient 208 employs controller 210 to set SCU 160 in a state where it delivers a prescribed stimulation pattern from a predetermined range of allowable stimulation patterns.

6. To cease electrical and/or drug stimulation, patient 208 employs controller 210 to turn off SCU 160.

7. Periodically, the patient or caregiver recharges the power source/storage device 166 of SCU 160, if necessary, in accordance with Function 1 described above (i.e., transmit electrical power).

For the treatment of any of the various types and severities of movement disorders, it may be desirable to modify or adjust the algorithmic functions performed by the implanted and/or external components, as well as the surgical approaches, in ways that would be obvious to skilled practitioners of these arts. For example, in some situations, it may be desirable to employ more than one SCU 160, each of which could be separately controlled by means of a digital address. Multiple channels and/or multiple patterns of electrical and/or drug stimulation might thereby be programmed by the clinician and controlled by the patient in order to, for instance, deal with complex or multiple symptoms or conditions, such as Parkinson's disease coupled with side effects from medication, e.g., dyskinesia.

In some embodiments discussed earlier, SCU 160, or a group of two or more SCUs, is controlled via closed-loop operation. A need for and/or response to stimulation is sensed via SCU 160, or by an additional SCU (which may or may not be dedicated to the sensing function), or by another implanted or external device. If necessary, the sensed information is transmitted to SCU 160. In some cases, the sensing and stimulating are performed by one SCU. In some embodiments, the parameters used by SCU 160 are automatically adjusted based on the sensed information. Thus, the electrical and/or drug stimulation parameters are adjusted in a closed-loop manner to provide stimulation tailored to the need for and/or response to the electrical and/or drug stimulation.

Figure 7:
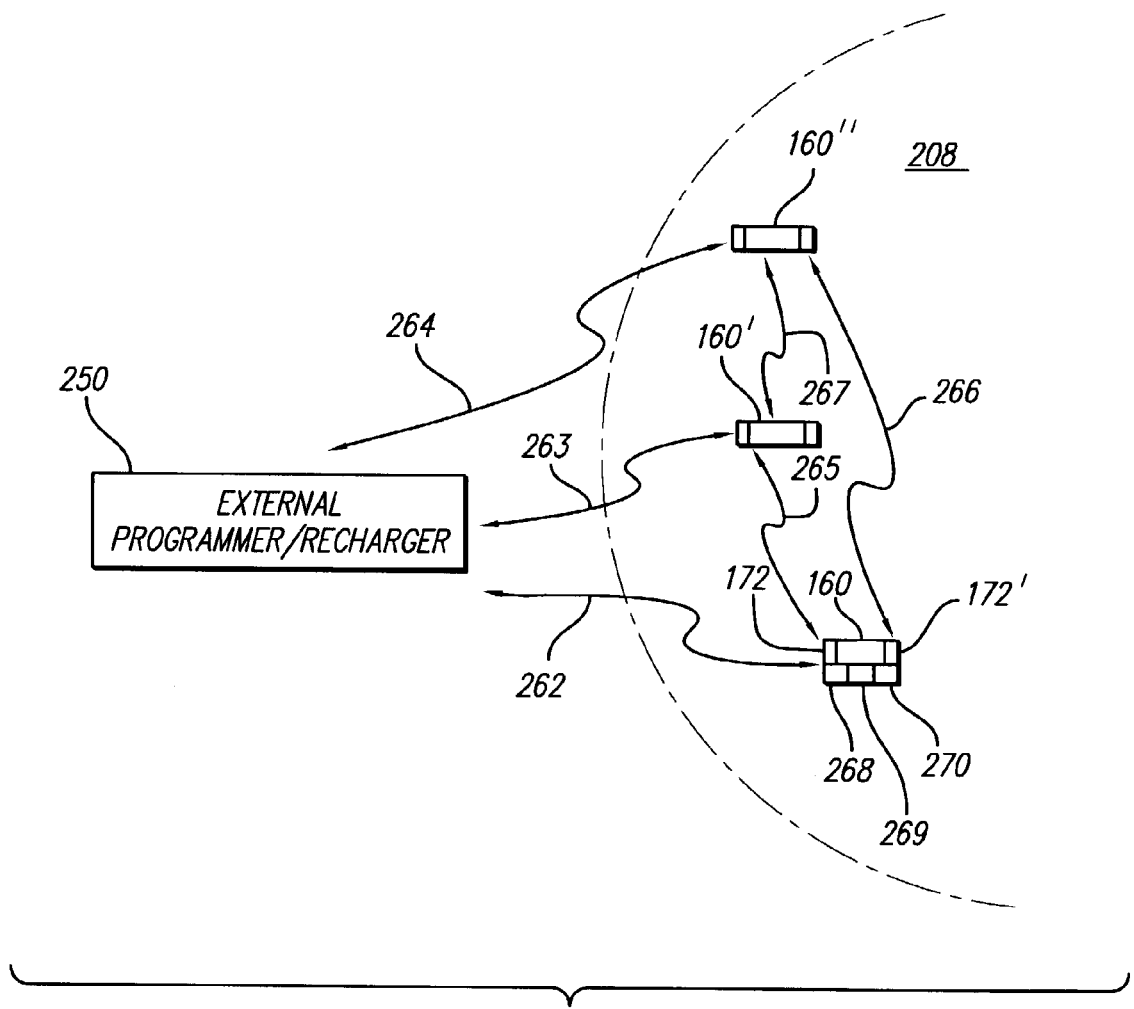
FIG. 7 depicts a system of implantable devices that communicate with each other and/or with external control/programming devices.

For instance, as shown in the example of FIG. 7, a first SCU 160, implanted beneath the skin of the patient 208, provides a first medication or substance; a second SCU 160' provides a second medication or substance; and a third SCU 160" provides electrical stimulation via electrodes 172 and 172'. As mentioned earlier, the implanted devices may operate independently or may operate in a coordinated manner with other similar implanted devices, other implanted devices, or other devices external to the patient's body, as shown by the control lines 262, 263 and 264 in FIG. 7. That is, in accordance with certain embodiments of the invention, the external controller 250 controls the operation of each of the implanted devices 160, 160' and 160". According to various embodiments of the invention, an implanted device, e.g. SCU 160, may control or operate under the control of another implanted device(s), e.g. SCU 160' and/or SCU 160". That is, a device made in accordance with the invention may communicate with other implanted stimulators, other implanted devices, and/or devices external to a patient's body, e.g., via an RF link, an ultrasonic link, a thermal link, an optical link, or the like. Specifically, as illustrated in FIG. 7, SCU 160, 160', and/or 160", made in accordance with the invention, may communicate with an external remote control (e.g., patient and/or physician programmer 250) that is capable of sending commands and/or data to implanted devices and that may also be capable of receiving commands and/or data from implanted devices.

A drug infusion stimulator made in accordance with the invention may incorporate communication means for communicating with one or more external or site-specific drug delivery devices, and, further, may have the control flexibility to synchronize and control the duration of drug delivery. The associated drug delivery device typically provides a feedback signal that lets the control device know it has received and understood commands. The communication signal between the implanted stimulator and the drug delivery device may be encoded to prevent the accidental or inadvertent delivery of drugs by other signals.

An SCU made in accordance with the invention thus incorporates, in some embodiments, first sensing means 268 for sensing therapeutic effects, clinical variables, or other indicators of the state of the patient, such as head acceleration, limb acceleration, limb EMG, and/or discharge frequency of a neural population, or the like. The stimulator additionally or alternatively incorporates second means 269 for sensing neurotransmitter levels and/or their associated breakdown product levels, medication levels and/or other drug levels, hormone, enzyme, ketone, electrolytes, interleukin, cytokine, lymphokine, chemokine, and/or growth factor levels and/or changes in these or other substances in the blood plasma, local interstitial fluid, and/or cerebrospinal fluid. The stimulator additionally or alternatively incorporates third means 270 for sensing electrical current levels and/or waveforms supplied by another source of electrical energy. Sensed information may be used to control infusion and/or electrical parameters in a closed loop manner, as shown by control lines 266, 267, and 265. Thus, the sensing means may be incorporated into a device that also includes electrical and/or drug stimulation, or the sensing means (that may or may not have stimulating means), may communicate the sensed information to another device(s) with stimulating means.

According to some embodiments of the invention, the electrical and/or drug stimulation decreases activity of one or more areas of the brain that exhibit chronic increased activity, relative to control subjects, in patients experiencing a movement disorder(s). These areas may include one or more of the pallido-thalamic axons 107, putamen to GPe fibers 108, and/or subthalamo-pallidal fibers. Such inhibitory stimulation is likely to be produced by relatively high-frequency electrical stimulation (e.g., greater than about 100–150 Hz), an excitatory neurotransmitter antagonist(s) (e.g. prazosin, metoprolol, atropine), an inhibitory neurotransmitter(s) (e.g., GABA), an agonist thereof, an agent that increases the level of an inhibitory neurotransmitter, an agent that decreases the level of an excitatory neurotransmitter (e.g., DCG-IV), a local anesthetic agent (e.g., lidocaine), and/or an analgesic medication. This stimulation may be applied to one or more of the pallido-thalamic axons 107, putamen to GPe fibers 108, and subthalamo-pallidal fibers to treat movement disorder(s).

According to other embodiments of the invention, the electrical and/or drug stimulation increases activity of one or more of those areas of the brain that exhibit chronic decreased activity, relative to control subjects, in patients experiencing a movement disorder(s), thereby treating or preventing such disorder(s) and/or the symptoms and/or pathological consequences thereof. These areas may include one or more of the NTS 100, pallido-subthalamic tracts 106, and putamen to GPi fibers. Such excitatory stimulation is likely to be produced by relatively low-frequency electrical stimulation (e.g., less than about 100–150 Hz), an excitatory neurotransmitter (e.g., glutamate, acetylcholine), an excitatory cortical neurotransmitter agonist (e.g., glutamate receptor agonist, L-aspartic acid, N-methyl-D-aspartic acid (NMDA), bethanechol, norepinephrine), an inhibitory neurotransmitter antagonist(s) (e.g., bicuculline), an agent that increases the level of an excitatory neurotransmitter (e.g., edrophonium), and/or an agent that decreases the level of an inhibitory neurotransmitter. This stimulation may be applied to one or more of the NTS 100, pallidosubthalamic tracts 106, and putamen to GPi fibers to treat movement disorder(s).

According to certain embodiments, the stimulation selectively increases neural activity of the relatively large diameter fibers of the nucleus tractus solitarius (NTS 100). Relatively low amplitude (e.g., about 0.05 mA to about 5.0 mA) electrical current pulses are likely to produce such selective excitation.

According to various embodiments, one or more stimulating drugs, possibly in combination with electrical stimulation, are infused into the brain. For instance, a growth factor, such as glial cell line-derived neurotrophic factor (GDNF) may be infused into the putamen 116, possibly while providing electrical stimulation as described above. Other stimulating drugs are described previously herein and include brain cell line-derived neurotrophic factor (BDNF), naloxone, and levodopa.

In various embodiments, sensing means described earlier may be used to orchestrate first the activation of SCU(s) targeting an area(s) of the brain, and then, when appropriate, SCU(s) targeting another area(s) and/or by different means. Alternatively, this orchestration may be programmed, and not based on a sensed condition.

While the invention herein disclosed has been described by means of specific embodiments and applications thereof, numerous modifications and variations could be made thereto by those skilled in the art without departing from the scope of the invention set forth in the claims.

What is claimed is:

1. A method of treating a patient with a movement disorder, comprising:
   implanting at least one system control unit entirely within the brain of the patient, wherein the at least one unit controls the delivery of at least one stimulus to at least one area of the brain affecting a movement disorder;
   applying the at least one stimulus to the at least one area of the brain in order to at least in part alleviate the movement disorder of the patient being treated; and
   applying the at least one stimulus to increase neural activity of the relatively large diameter fibers of the nucleus tractus solitarius (NTS);
   wherein the at least one system control unit is a microstimulator implanted entirely within the brain.

2. The method of claim 1 wherein the system control unit is connected to at least one electrode, and wherein the stimulus comprises electrical stimulation delivered via the at least one electrode.

3. The method of claim 1 wherein the system control unit is connected to at least one infusion outlet, and wherein the stimulus comprises stimulation via one or more drugs delivered through the at least one outlet.

4. The method of claim 1 wherein the system control unit is connected to at least one electrode and to at least one infusion outlet, and wherein the stimulus comprises both electrical stimulation delivered via the at least one electrode and stimulation via one or more drugs delivered through the at least one outlet.

5. The method of claim 1 further comprising sensing at least one condition and using the at least one sensed condition to automatically determine the stimulus to apply.

6. The method of claim 5 wherein the at least one sensed condition is at least one of head acceleration, limb acceleration, electrical activity of the brain, nerve activity, muscle activity, discharge frequency of a neural population, impedance, a neurotransmitter level, change in a neurotransmitter level, a neurotransmitter breakdown product level, change in a neurotransmitter breakdown product level, a hormone level, change in a hormone level, a ketone level, change in a ketone level, an interleukin level, change in an interleukin level, a cytokine level, change in a cytokine level, a lymphokine level, change in a lymphokine level, a chemokine level, change in a chemokine level, a growth factor level, change in a growth factor level, an electrolyte level, change in an electrolyte level, an enzyme level, change in an enzyme level, a medication level, change in a medication level, a drug level, change in a drug level, pH level, change in pH level, level of a bloodborne substance, and change in level of a bloodborne substance.

7. The method of claim 1 wherein the stimulating pulses are at least electrical pulses applied at less than about 0.05 to about 5.0 mA.

8. A method of treating a patient with a movement disorder, comprising:
   providing at least one system control unit that generates stimulating pulses in accordance with prescribed parameters, which stimulating pulses are at least one of infusion pulses and electrical stimulation pulses;
   providing, connected to the at least one system control unit, at least one catheter with at least one discharge portion or at least one lead with at least one electrode;
   implanting at least one of the at least one discharge portion and the at least one electrode adjacent to at least one brain structure affecting a movement disorder;
   implanting at least one system control unit in the patient, wherein the at least one unit controls the delivery of the stimulating pulses applied to the at least one brain structure to be stimulated;
   tunneling at least one of the at least one catheter and the at least one lead between the at least one brain structure and the system control unit location;
   applying the stimulating pulses to increase activity of the at least one brain structure in order to at least in part alleviate the movement disorder of the patient being treated; and
   wherein the at least one brain structure is at least one of the nucleus tractus solitarius (NTS), pallido-subthalamic tracts, and putamen to GPi fibers.

9. The method of claim 8 wherein the stimulating pulses are at least relatively low-frequency electrical pulses applied at less than about 100–150 Hz.

10. The method of claim 8 wherein the stimulating pulses are at least infusion pulses of at least one of an excitatory neurotransmitter, an excitatory cortical neurotransmitter agonist, an inhibitory neurotransmitter antagonist, an agent that increases the level of an excitatory neurotransmitter, and an agent that decreases the level of an inhibitory neurotransmitter.

11. The method of claim 8 further comprising applying the stimulating pulses to increase neural activity of the relatively large diameter fibers of the nucleus tractus solitarius (NTS), wherein the stimulating pulses are at least electrical pulses applied at less than about 0.05 to about 5.0 mA.

12. The method of claim 8 further comprising sensing at least one condition and using the at least one sensed condition to automatically determine the stimulating pulses to apply.

13. The method of claim 12 wherein the at least one sensed condition is at least one of head acceleration, limb acceleration, electrical activity of the brain, nerve activity, muscle activity, discharge frequency of a neural population, impedance, a neurotransmitter level, change in a neurotransmitter level, a neurotransmitter breakdown product level, change in a neurotransmitter breakdown product level, a hormone level, change in a hormone level, a ketone level, change in a ketone level, an interleukin level, change in an interleukin level, a cytokine level, change in a cytokine level, a lymphokine level, change in a lymphokine level, a chemokine level, change in a chemokine level, a growth factor level, change in a growth factor level, an electrolyte level, change in an electrolyte level, an enzyme level, change in an enzyme level, a medication level, change in a medication level, a drug level, change in a drug level, pH level, change in pH level, level of a bloodborne substance, and change in level of a bloodborne substance.

14. A method of treating a patient with a movement disorder, comprising:
providing at least one system control unit that generates stimulating pulses in accordance with prescribed parameters, which stimulating pulses are at least one of infusion pulses and electrical stimulation pulses;
providing, connected to the at least one system control unit, at least one catheter with at least one discharge portion or at least one lead with at least one electrode;
implanting at least one of the at least one discharge portion and the at least one electrode adjacent to at least one brain structure affecting a movement disorder;
implanting at least one system control unit in the patient, wherein the at least one unit controls the delivery of the stimulating pulses applied to the at least one brain structure to be stimulated;
tunneling at least one of the at least one catheter and the at least one lead between the at least one brain structure and the system control unit location;
applying the stimulating pulses to decrease activity of the at least one brain structure in order to at least in part alleviate the movement disorder of the patient being treated; and
wherein the at least one brain structure is at least one of the pallido-thalamic axons, putamen to GPe fibers, and subthalamo-pallidal fibers.

15. The method of claim 14 wherein the stimulating pulses are at least relatively high-frequency electrical pulses applied at greater than about 100–150 Hz.

16. The method of claim 14 wherein the stimulating pulses are at least infusion pulses of at least one of an excitatory neurotransmitter antagonist, an inhibitory neurotransmitter, an inhibitory neurotransmitter agonist, an agent that increases the level of an inhibitory neurotransmitter, an agent that decreases the level of an excitatory neurotransmitter, a local anesthetic agent, and an analgesic medication.

17. The method of claim 14 further comprising sensing at least one condition and using the at least one sensed condition to automatically determine the stimulating pulses to apply.

18. The method of claim 17 wherein the at least one sensed condition is at least one of head acceleration, limb acceleration, electrical activity of the brain, nerve activity, muscle activity, discharge frequency of a neural population, impedance, a neurotransmitter level, change in a neurotransmitter level, a neurotransmitter breakdown product level, change in a neurotransmitter breakdown product level, a hormone level, change in a hormone level, a ketone level, change in a ketone level, an interleukin level, change in an interleukin level, a cytokine level, change in a cytokine level, a lymphokine level, change in a lymphokine level, a chemokine level, change in a chemokine level, a growth factor level, change in a growth factor level, an electrolyte level, change in an electrolyte level, an enzyme level, change in an enzyme level, a medication level, change in a medication level, a drug level, change in a drug level, pH level, change in pH level, level of a bloodborne substance, and change in level of a bloodborne substance.

* * * * *